US010967025B2

(12) United States Patent
Vieira

(10) Patent No.: US 10,967,025 B2
(45) Date of Patent: Apr. 6, 2021

(54) HERBAL NUTRACEUTICAL FORMULATION TO REDUCE OXIDATIVE STRESS, VIRAL AND MICROBIAL INFECTIONS, AND INFLAMMATION

(71) Applicant: Moringo Organics Inc., Farmingville, NY (US)

(72) Inventor: Karen Vieira, West Palm Beach, FL (US)

(73) Assignee: Moringo Organics Inc., Bohemia, NY (US)

( * ) Notice: Subject to any disclaimer, the term of this patent is extended or adjusted under 35 U.S.C. 154(b) by 441 days.

(21) Appl. No.: 15/563,617

(22) PCT Filed: Jun. 1, 2017

(86) PCT No.: PCT/IB2017/053243
§ 371 (c)(1),
(2) Date: Oct. 2, 2017

(87) PCT Pub. No.: WO2018/220428
PCT Pub. Date: Dec. 6, 2018

(65) Prior Publication Data
US 2019/0209634 A1 Jul. 11, 2019

(51) Int. Cl.
| | | |
|---|---|---|
| *A61K 36/00* | (2006.01) |
| *A61K 36/31* | (2006.01) |
| *A61K 36/9066* | (2006.01) |
| *A61K 36/185* | (2006.01) |
| *A61K 36/48* | (2006.01) |
| *A61K 36/53* | (2006.01) |
| *A61K 36/67* | (2006.01) |
| *A61K 35/74* | (2015.01) |
| *A61K 36/47* | (2006.01) |
| *A61P 39/06* | (2006.01) |
| *A61P 3/06* | (2006.01) |
| *A61P 3/10* | (2006.01) |
| *A61K 9/00* | (2006.01) |
| *A61K 9/48* | (2006.01) |
| *A61K 31/4525* | (2006.01) |
| *A61K 35/04* | (2006.01) |
| *A61K 35/748* | (2015.01) |
| *A61K 36/61* | (2006.01) |

(52) U.S. Cl.
CPC ............ *A61K 36/31* (2013.01); *A61K 9/0053* (2013.01); *A61K 9/48* (2013.01); *A61K 31/4525* (2013.01); *A61K 35/04* (2013.01); *A61K 35/74* (2013.01); *A61K 35/748* (2013.01); *A61K 36/185* (2013.01); *A61K 36/47* (2013.01); *A61K 36/48* (2013.01); *A61K 36/53* (2013.01); *A61K 36/61* (2013.01); *A61K 36/67* (2013.01); *A61K 36/9066* (2013.01); *A61P 3/06* (2018.01); *A61P 3/10* (2018.01); *A61P 39/06* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 6,042,834 A | 3/2000 | Baraka | |
| 6,264,995 B1 * | 7/2001 | Newmark | ............ A61K 36/29 424/725 |
| 6,541,045 B1 | 4/2003 | Charters et al. | |

OTHER PUBLICATIONS

Kumar et al. (2013) Journal of Ocular Pharmacology and Therapeutics, vol. 29, No. 4: 419-426. (Year: 2013).*
Agarwal et al. (2007) Phytother. Res. 21, 401-405. (Year: 2007).*
Ismail et al. (2015) Biomed. Res. International, vol. 2015, ID 486120, 7 pages (Year: 2015).*
Poltanov et al. (2009) Phytother. Res. 23: 1309-1315. (Year: 2009).*
Kaviarasan et al. (2004) Plant Foods for Human Nutrition 59: 143-147. (Year: 2004).*
Selvam et al. (1995) J. Ethnopharmacol. 47: 59-67. (Year: 1995).*
Panahi et al. (2015) Clinical Nutrition, 34: 1101-1108. (Year: 2015).*
Russ, K., Antioxidants: The natural anti-inflammatory. 2014.
Reuter S, Gupta SC, Chaturvedi MM, Aggarwal BB., Oxidative stress, inflammation, and cancer: how are they linked? Free Radic Biol Med. 2010; 49(11):1603-16.
Durackova Z. Some current insights into oxidative stress. Physiol Res. 2010; 59(4):459-69. Poyton RO, Ball KA, Castello PR. Mitochondrial generation of free radicals and hypoxic signaling. Trends Endocrinol Metab. 2009; 20(7):332-40.
Poyton RO, Ball KA, Castello PR., Mitochondrial generation of free radicals and hypoxic signaling. Trends Endocrinol Metab. 2009; 20(7):332-40.
Fridovich I. The biology of oxygen radicals. Science. 1978; 201 (4359):875-80.
Goossens V, De Vos K, Vercammen D, Steemans M, Vancompernolle K, Fiers W, Vandenabeele P, Grooten J. Redox regulation of TNF signaling. Biofactors. 1999; 10(2-3):145-56.

(Continued)

Primary Examiner — Russell G Fiebig
(74) Attorney, Agent, or Firm — Trojan Law Offices

(57) ABSTRACT

The main objective of the present invention is to develop an herbal formulation with high polyphenol concentrations. A therapeutic effect of ingredients in herbal composition with Antioxidants, Anti-inflammatories, Anti Viral & Anti Microbial properties to reduce Oxidative Stress, Inflammation, Viral and Microbial Infections. The herbal composition promotes management of diabetes, regulation of cholesterol, also immune system processes that helps to fight against viral and bacterial infections, colds, or the flu, skin ailments such as Psoriasis & eczema. Herbal Composition comprises synergistic combination of *Moringa Oleifera* Leaf Powder, Spirulina & Aqueous extracts of Oregano Vulgare Leaf Extract, Shilajit extract, Rosemary Leaf extract, Pomegranate Fruit Preel extract, Amla fruit extract, Fenugreek Seed Extract, Curcumin Extract, Piperine extract. Therefore, the chosen herbal blend provides the body with all of the vitamins, minerals, and nutrients it needs to continuously boost health.

3 Claims, 18 Drawing Sheets

(56) References Cited

OTHER PUBLICATIONS

Hussain SP, Hofseth LJ, Harris CC., Radical causes of cancer. Nat Rev Cancer. 2003; 3(4):276-85.
Schraufstatter I, Hyslop PA, Jackson JH, Cochrane CG., Oxidant-induced DNA damage of target cells. J Clin Invest. 1988; 82(3):1040-50.
Visconti R, Grieco D., New insights on oxidative stress in cancer. Curr Opin Drug Discov Devel. 2009; 12(2):240-5.
Briganti S, Picardo M., Antioxidant activity, lipid peroxidation and skin diseases. What's new. J Eur Acad Dermatol Venereal. 2003; 17(6):663-9.
Chaturvedi N., The burden of diabetes and its complications: trends and implications for intervention. Diabetes Res Clin Pract May 2007; 76 Suppl 1():S3-12.
Brownlee M., Biochemistry and molecular cell biology of diabetic complications. Nature. 2001; 414(6865):813-20.
Godsey J, Grundmann 0., Review of Various Herbal Supplements as Complementary Treatments for Oral Cancer. J Diet Suppl. 2016; 1-13, in press.
Kumar Gupta S, Kumar B, Srinivasan BP, et al., Retinoprotective effects of Moringa oleifera via antioxidant, anti-inflammatory, and anti-angiogenic mechanisms in streptozotocin-induced diabetic rats. J Ocul Pharmacol Ther. May 2013;29(4):419-26.
Fahey JW., Moringa oleifera: A review of the medical evidence for its nutritional, therapeutic, and prophylactic properties. Part 1. Trees for Life Journal 2005;1 :5.
Dragland S, Senoo H, Wake K, Holte K, Blomhoff R, Several Culinary and Medicinal Herbs Are Important Sources of Dietary Antioxidants. JNutr 2003;133(5):1286-1290.
Moreno S. Scheyer T, Romano CS, Vojnov AA., Antioxidant and antimicrobial activities of rosemary extracts inked to their polyphenol composition. Free Radie Res. 2006;40(2):223-31.
Cheung S, Tai J., Anti-proliferative and antioxidant properties of rosemary *Rosmarinus officinalis*. Oncology Reports. 2007; 17(6):1525-31.
Peng CH, Su JD, Chyau CC, Sung TY, Ho SS, Peng CC, Peng RY., Supercritical fluid extracts of rosemary leaves exhibit potent anti-inflammation and anti-tumor effects. Biosci Biotechnol Biochem. 2007; 71 (9):2223-32.
Fawole OA, Makunga NP, Opara UL., Antibacterial, antioxidant and tyrosinase-inhibition activities of pomegranate fruit peel methanolic extract. BMC Complement Altern Med. 201230; 12:200.
Neyrinck AM, Van Hee VF, Bindels LB, et al., Polyphenol rich extract of pomegranate peel alleviates tissue inflammation and hypercholesterolaemia in high-fat diet-induced obese mice: potential implication of the gut microbiota. BrJ Nutr. Mar. 14, 2013;109(5):802-9.
Poltanov EA, Shikov AN, Dorman HJ, Pozharitskaya ON, Makarov VG, Tikhonov VP, Hiltunen R., Chemical and antioxidant evaluation of Indian gooseberry (*Emblica officinalis* Gaertn, syn. *Phyllanthus emblica* L) supplements. Phytother Res. 2009;23(9)1309-15.
Kim HJ, Yokozawa T, Kim HY, Tohda C, Rao TP, Juneja LR., Influence of amla (*Emblica officinalis* Gaertn.) on hypercholesterolemia and lipid peroxidation in cholesterol-fed rats. J Nutr Sci Vitaminol (Tokyo). 2005;51 {6}:413-8.
Mahata S, Pandey A, Shukla S, Tyagi A, Husain SA, Das BC, Bharti AC., Anticancer activity of *Phyllanthus emblica* Linn. (Indian 15 gooseberry): inhibition of transcription factor AP-1 and HPV gene expression in cervical cancer cells. Nutr Cancer. 2013;65 Suppl 1:88- 97.
Koshy SM, Bobby Z, Hariharan AP, Gopalakrishna SM., Amla (*Emblica officinalis*) extract is effective in preventing high fructose diet-induced 20 insulin resistance and atherogenic dyslipidemic profile in ovariectomized female albino rats. Menopause. 2012;19(10):1146-55.

D'Souza JJ, D'Souza PP, Fazal F, Kumar A, Bhat HP, Baliga MS. Anti-diabetic effects of the Indian indigenous fruit *Emblica officinalis* Gaertn: active constituents and modes of action. Food Funct. 2014;5(4):635-44.
Akhtar MS, Ramzan A, Ali A, Ahmad M., Effect of Amla fruit (*Emblica officinalis* Gaertn.) on blood glucose and lipid profile of normal subjects and type 2 diabetic patients. Int J Food Sci Nutr. Sep. 2011;62(6):609-16. doi: 10.3109/09637486.2011.560565. Epub Apr. 18, 2011.
Park, S., et al., Anti-Inflammatory Effects of Pomegranate Peel Extract in THP-1 Cells Exposed to Particulate Matter PM10—Soojin Park Evidence-Based Complementary and Alternative Medicine vol. 2016 {2016), Article ID 6836080.
Mazokopakis EE, Starakis IK, Papadomanolaki MG, Mavroeidi NG, Ganotakis ES., The hypolipidaemic effects of Spirulina (*Arthrospira platensis*) supplementation in a Cretan population: a prospective study. J Sci Food Agric. 2014;94(3):432-7.
Torres-Duran PV, Ferreira-Hermosillo A, Juarez-Oropezaco MA., Antihyperlipemic and antihypertensive effects of Spirulina maxima in an open sample of mexican population: a preliminary report. Lipids Health Dis. 2007; 6: 33.
Park HJ, Lee YJ, Ryu HK, Kim MH, Chung HW, Kim WY., A randomized double-blind, placebo-controlled study to establish the effects of spirulina in elderly Koreans. Ann Nutr Metab. 2008;52(4):322-8.
Parikh P, Mani U, Iyer U. Role of Spirulina in the Control of Glycemia and Lipidemia in Type 2 Diabetes Mellitus. J Med Food. 2001;4(4):193-199.
Ismail M, Hossain MF, Tanu AR, Shekhar HU., Effect of Spirulina Intervention on Oxidative Stress, Antioxidant Status, and Lipid Profile in Chronic Obstructive Pulmonary Disease Patients. Biomed Res Int. 2015;2015:486120.
Ku CS, Yang Y, Park Y, Jiyoung L., Health Benefits of Blue-Green Algae: Prevention of Cardiovascular Disease and Nonalcoholic Fatty Liver Disease. J Med Food. 2013; 16(2): 103-111.
Lee EH,Park JE,Choi YJ,Huh KP, Wha-Young K., A randomized study to establish the effects of spirulina in type 2 diabetes mellitus patients. Nutr Res Pract. 2008; 2(4): 295-300.
Kalafati M, Jamurtas AZ, Nikolaidis MG, Paschalis V, Theodorou AA, Sakellariou GK, Koutedakis Y, Kouretas D., Ergogenic and antioxidant effects of spirulina supplementation in humans. Med Sci Sports Exerc. 2010;42(1):142-51.
Tayyem RF, Heath DD, Al-Delaimy WK, Rock CL., Curcumin content of turmeric and curry powders. Nutr Cancer. 2006;55(2):126-31.
Shoba G, Joy D, Joseph T, Majeed M, Rajendran R, Srinivas PS., Influence of piperine on the pharmacokinetics of curcumin in animals and human volunteers. Planta Med. 1998;64(4):353-6.
Jurenka JS., Anti-inflammatory properties of curcumin, a major constituent of Curcuma longa: a review of preclinical and clinical research. Altern Med Rev. 2009;14(2):141-53.
Singh S, Aggarwal BB., Activation of Transcription Factor NF-KB Is Suppressed by Curcumin (Diferuloylmethane). J Bio Chem. 1995; 270:24995-25000.
Marin YE, Wall BA, Wang S, Namkoong J, Martino JJ, Suh J, Lee HJ, Rabson AB, Yang CS, Chen S, Ryu JH., Curcumin down regulates the constitutive activity of NF-kappaB and induces apoptosis in novel mouse melanoma cells. Melanoma Res. 2007;17(5)274-83.
Chainani-Wu N., Safety and anti-inflammatory activity of curcumin: a component of tumeric (*Curcuma longa*). J Altern Complement Med. Feb. 2003;9(1):161-8.
Goel A, Boland CR, Chauhan DP., Specific inhibition of cyclooxygenase-2 (COX-2) expression by dietary curcumin in HT-29 human colon cancer cells. Cancer Lett. 2001 ;172(2):111-8.
Aggarwal BB, Harikumar KB., Potential therapeutic effects of curcumin, the anti-inflammatory agent, against neurodegenerative, cardiovascular, pulmonary, metabolic, autoimmune and neoplastic diseases. Int J Biochem Cell Biol. 2009;41 (1 ):40-59.
Bano G, Amla V, Raina RK, et al., The effect of piperine on pharmacokinetics of phenytoin in healthy volunteers. Planta Med 1987;53:568-9.

(56) References Cited

OTHER PUBLICATIONS

Khardwaj RK, Glaeser H, Becquemont L, et al., Pipeline, a major constituent of black pepper, inhibits human P-glycoprotein and CYP3A4. J Pharmacol Exp Ther 2002;302:645-50.

Shrivastava P, Vaibhav K, Tabassum R, et al., Anti-apoptotic and anti- inflammatory effect of Pipeline on 6-0H DA induced Parkinson's rat model. J Nutr Biochem. Apr. 2013;24(4):680.

Ceriello A, Testa R., Antioxidant anti-inflammatory treatment in type 2 diabetes. Diabetes Care. 2009;32 Suppl 2: S232-6.

Abourashed EA., Bioavailability of Plant-Derived Antioxidants. Antioxidants (Basel). 2013;2(4):309-25.

Srichamroen A., et al., The Modifying Effects of Galactomannan from Canadian-Grown Fenugreek (*Trigonella benum-graecum* L) on the Glycemic and Lipidemic Status in Rats Anchalee Srichamroen J Clin Biochem Nutr. Nov. 2008; 43(3): 167-174.

\* cited by examiner

HERBAL NUTRACEUTICAL FORMULATION TO REDUCE OXIDATIVE STRESS, VIRAL AND MICROBIAL INFECTIONS, AND INFLAMMATION

FILED OF THE INVENTION

The present invention relates to a therapeutic herbal composition to reduce oxidative stress & inflammation. Also, directed to the development of different compositions to regulate blood sugar, blood cholesterol, to treat cold, flu & skin ailments such as Psoriasis & eczema

BACKGROUND OF THE INVENTION

The invention pertains to the formulation, development, and preparation of aqueous extracts derived from phytochemical compounds for an herbal supplement. More particularly, the invention serves the purposes of herbal supplementation.

Herbal supplements generally contain substances that support one or two bodily systems, but various supplements have to be acquired in order to support whole body health. This invention provides the body with a continuous supply of the right combination of vitamins, minerals, nutrients, and antioxidants that promote optimal long-term health for all of the body's systems. This is an invention that bypasses the need of having to acquire several different supplements to reap the same types of health benefits.

Inflammation & Oxidative Stress

Inflammation is one of several health problems that is caused by free radical damage. Free radicals are unstable oxygen-containing particles that have destructive effects on the body's cells. The body's immune system normally stimulates the release of cells that, along with antioxidants supplied through food or dietary supplements, work to remove free radicals from the body. When free radical levels increase excessively, cell damage, also known as oxidative stress, can occur. Oxidative stress refers to an imbalance between the rapid production of free radicals and the body's ability to use antioxidants to detoxify or neutralize the destructive effects. The body produces a certain amount of antioxidants, such as peroxidase enzyme, catalase, and superoxide dismutase, naturally, but the level is not typically high enough to detoxify the body of all free radicals that may be circulating.

Uncontrolled free radical levels and oxidative stress leads to chronic inflammation. The development of many degenerative diseases, including heart disease, diabetes, cancer, arthritis, Alzheimer's and Multiple Sclerosis (MS), among others, are directly associated with chronic inflammation. The area in which the most free radical damage occurs generally determines the type of degenerative disease that will develop. For instance, excessive free radical damage of the joints may lead to osteoarthritis, while this form of damage in the brain may result in the onset of Alzheimer's, etc.

Research has shown that feeding people a meal that is either high in "bad" fats or has a high glycemic index leads to the production of increased free radical levels. The free radicals cause inflammation in the lining of the arteries, which makes them spasm. In some persons, eating just one of these types of meals may cause arterial spasms that can last for 4-5 hours. This type of abnormal blood vessel activity is detrimental toward good health. In the same study, when the participants were give antioxidants before one of the meals, arterial spasms only occurred for 4-5 minutes. This is a dramatic difference that can be attributed to the antioxidants' ability to neutralize the free radicals before they could cause inflammatory damage. Persistent inflammation of the blood vessels is the first stage of heart disease and it may start very early in life.

Extensive research during the last two decades has also revealed the mechanism by which continued oxidative stress can lead to chronic inflammation that can in turn, lead to the onset of chronic diseases such as cancer and diabetes as well as cardiovascular, neurological, and pulmonary diseases. Oxidative stress can activate a variety of transcription factors or proteins, including: nuclear factor kappa B (NF-κB), hypoxia-inducible factor-1a (HIF1-α), activator protein-1 (AP-1), peroxisome proliferator-activated receptor-γ (PPAR-γ), NF-E2 related factor-2 (Nrf2), β-catenin/Wnt, and p53 [4]. Activation of these transcription factors can lead to the expression of over 500 different genes, including those for growth factors, inflammatory cytokines, chemokines, cell cycle regulatory molecules, and anti-inflammatory molecules.

How oxidative stress activates inflammatory pathways and leads to the transformation of a normal cell into a tumor cell, as well as the facilitation of tumor cell survival, proliferation, chemo-resistance, radio-resistance, invasion, angiogenesis, and stem cell survival, is the focus of this review in regard to this invention. Overall, observations to date suggest that oxidative stress, chronic inflammation, and cancer are actually closely linked.

Oxidative stress occurs as a result of an imbalance between the production of free radicals and reactive metabolites called oxidants or reactive oxygen species (ROS), and their elimination by protective mechanisms such as antioxidants. The disproportion leads to damage of important biomolecules and cells that can potentially impact the whole organism. ROS are by-products of normal cellular metabolism and they play vital roles in the stimulation of signaling pathways in plant and animal cells in response to changes of intra- and extracellular environmental conditions. Most ROS are generated in cells by the mitochondrial respiratory chain During endogenous metabolic reactions, aerobic cells produce ROS that include: superoxide anion ($O_2-$), hydrogen peroxide ($H_2O_2$), hydroxyl radical (OH•), and organic peroxides as normal by-products of the biological reduction of molecular oxygen. The transfer of an electron to molecular oxygen occurs as a result of the respiratory chain process, and the electron transport chains are located in membranes of the mitochondria. Under hypoxic conditions, the mitochondrial respiratory chain also produces nitric oxide (NO), which can generate other reactive nitrogen species (RNS). RNS, subsequently leads to the production of additional reactive species such as reactive aldehydes-malondialdehyde (MDA) and 4-hydroxynonenal (4-HNE), by inducing excessive lipid peroxidation. Proteins and lipids are also significant targets for oxidative attack, and the modification of these molecules can increase the risk of mutagenesis.

Under a sustained form of environmental stress, ROS will be produced over a long period of time and thusly, significant damage may occur to cellular structures and functions, which may induce somatic mutations and neoplastic transformations. Indeed, the initiation and progression of cancer has been linked to oxidative stress due to the increase in DNA mutations or damage as well as genome instability and cell proliferation that ROS cause.

The skin, for example, is chronically exposed to both endogenous and environmental ROS due to its interface function between the body and the environment. Therefore, the skin needs a well-organized system of both chemical and enzymatic antioxidants in order to protect itself against this overload of oxidant species. The lungs, which are directly exposed to oxygen concentrations that are higher than in most other tissues, are protected against these oxidants by a variety of antioxidant mechanisms as well. Furthermore, aging, which is considered to be the result of an impairment of body functions over time due to the accumulation of molecular damage in DNA, proteins, and lipids, is also characterized by an increase in intracellular oxidative stress as a result of the progressive decrease of the intracellular ROS scavenging. Acting to protect the organism against these harmful ROS is a complex system of enzymatic antioxidants such as superoxide dismutase (SOD), glutathione peroxidase (GPx), glutathione reductase and catalase, as well as non-enzymatic antioxidants that include glutathione (GSH), vitamin C, and vitamin D. The inadequate supply of protective antioxidants that can detoxify ROS is associated with cellular damage that may lead to the onset of various conditions including cancer, diseases of the skin or major organs (e.g., lungs, heart), and even metabolic imbalances that can initiate the onset of diabetes.

Central Role of Oxidative Stress in the Pathogenesis of Diabetic Complications

The occurrence of type 2 diabetes has rapidly increased internationally during the last few decades, and it is estimated that the number of patients with this condition will more than double within 15 years. Type 2 diabetes mellitus is the most common form of diabetes and it is mainly characterized by the development of increased morbidity and mortality for cardiovascular disease (CVD); thusly, it has been suggested that diabetes may be considered to be a form of CVD. However, diabetes is also characterized by dramatic microangiopathic complications and nerve damage such as retinopathy, nephropathy, and neuropathy. Recent evidence indicates that glucose overload, which is one of the main occurrences observed with diabetes, may cause this type of damage by inducing oxidative stress. This is currently the basis of the "unifying hypothesis" that hyperglycemia-induced oxidative stress may account for the pathogenesis of all diabetic complications.

It is proposed that the following four key biochemical changes that develop as a result of hyperglycemia are all activated by a common mechanism that is the overproduction of superoxide radicals. In particular the four changes include: 1) increased flux through the polyol pathway (in which glucose is reduced to sorbitol, thereby decreasing the levels of both nicotinamide adenine dinucleotide phosphate (NADPH) and glutathione); 2) increased formation of advanced glycation end products (AGEs); 3) activation of protein kinase C (with effects ranging from vascular occlusion to the expression of pro-inflammatory genes), and 4) increased shunting of excess glucose through the hexosamine pathway (mediating the increased transcription of inflammatory cytokine genes).

Furthermore, excess plasma glucose drives the overproduction of electron donors, mainly nicotinamide adenine dinucleotide/Hydrogen (–NADH/H+), from the tricarboxylic acid cycle. This process in turn, results in the transfer of single electrons, instead of the usual electron pairs, to oxygen, which produces superoxide radicals and other reactive oxygen species instead of the usual water (H2O) end product. The superoxide anion itself inhibits the activity of the key glycolytic enzyme glyceraldehyde-3-phosphate dehydrogenase (GADPH), and consequently, glucose and glycolytic intermediates spill into the polyol and hexosamine pathways, as well as additional pathways that culminate in protein kinase C activation and intracellular AGE formation. The end result is progressive damage to various cellular structures in the body due to the cascade of destructive events that are associated with the oxidative stress that diabetes causes.

Role of Viruses and Bacteria in the Pathogenesis of Various Conditions

Exposure to viruses or bacteria are related to the silencing of genes that support the acute phase of immunity called inflammation, especially if nutrients and antioxidants are not present to facilitate the rapid removal of such microorganisms from the body. Acute inflammation is often beneficial if it does not become chronic because it stimulates the activation of bodily processes, specifically white blood cell activity, that destroys and removes harmful substances before they can begin to cause serious health problems. However, the rapid replication of viruses or the overproduction of bacteria can turn off genes that support these processes. People generally become more susceptible to conditions such as cancer and heart disease if this occurs. The genes that are involved in the body's response to viral infections, germs, and allergens can also be turned off due to chronic stress.

In particular, there is now sufficient evidence of carcinogenicity in humans for human T-cell lymphotrophic virus, human immunodeficiency virus, hepatitis B virus, hepatitis C virus, human papillomavirus, Epstein-Barr virus, and human herpes virus 8, according to the International Agency for Research on Cancer (IARC). Many other causes of cancer have also been identified by the IARC, which include: bacteria, sunlight, tobacco, pharmaceuticals, hormones, alcohol, parasites, fungi, salted fish, wood dust, and herbs. The World Cancer Research Fund and the American Institute for Cancer Research have determined additional causes of cancer, which include red meat, processed meats, low fiber diets, obesity, and sedentary lifestyles. Supplementation with antioxidants has been suggested to decrease cancer cell replication and increase chance of remission.

Herbal Compositions composed of natural ingredients and said to be useful in reducing Oxidative stress, Inflammation and blood sugar are disclosed.

For instance, U.S. Pat. No. 6,264,995 (Thomas Newmark, Paul Schulick) discloses an herbal composition reducing inflammation in bones and joints by inhibiting the enzyme cyclooxygenase-2 is prepared from holy basil, turmeric, ginger, green tea, rosemary, huzhang, Chinese goldthread, barberry, oregano and *scutellariae baicalensis*. More particularly, the herbal composition of the invention contains therapeutically effective amounts of the supercritical extracts of ginger, rosemary and oregano, and therapeutically effective amounts of extracts of holy basil, turmeric, green tea, huzhang, Chinese goldthread, barberry, rosemary and *scutellariae baicalensis*. the herbal composition contains organic anti-aging constituents that inactivate oxygen free radicals, thereby providing antioxidant benefits in addition to anti-inflammatory benefits.

U.S. Pat. No. 6,541,045 (Alec Charters, James Selander, Shayne Morris, Robert Charles Thompson, Lori Blackner) discloses an herbal composition for combating inflammation, comprising therapeutically effective amounts of Japanese knotweed, Devil's claw, grapeskin, and syzygium is provided. Also provided is an herbal composition for treating a cough and/or common cold, comprising therapeutically effective amounts of Japanese knotweed, lobelia, echinacea, slippery elm, Devil's claw, adhatoda, vitamin C, grapeskin, and syzygium. An herbal composition for alleviating menstrual discomfort, comprising therapeutically effective amounts of Japanese knotweed, chaste tree berry, Mexican wild yam, dandelion, Devil's claw, grapeskin, and syzygium is provided.

U.S. Pat. No. 6,042,834 (Mohamed Wasif Baraka) discloses an An herbal composition for the treatment of diabetes, comprising 15 percent by weight of dried, powdered seeds of *Trigonella foenum-graecum;* 23 percent by weight of dried, powdered seeds of *Nigella sativa;* 10 percent by weight of dried, powdered leaves of *Origanum vulgare;* 10 percent by weight of dried, powdered sap of *Rosmarinus officinalis;* 15 percent by weight of dried, powdered beans of *Lupinus termis;* 12 percent by weight of dried, powdered black leaves of *Lawsonia inermis*; and 15 percent by weight of dried, powdered seeds of *Foeniculum vulgare*. The herbal composition may be administered in non-encapsulated powder form or in capsule form However, there is a need to develop herbal compositions to provide maximum benefits for the consumers to improve health and enhance the ability to overcome various disease conditions naturally to regulate Inflammation, Oxidative Stress, CVD, blood sugar, cholesterol, Cold, Cough, Flu, indigestion; fatigue; infertility, Ulcers, Anemia, Skin ailments such as Psoriasis, Eczema. It is therefore the object of the present invention to provide the human body with a continuous supply of the combination of vitamins, minerals, Phytonutrients, Anti-inflammatory antioxidants, Antiviral that promote optimal long-term health for all of the body's systems.

SUMMARY OF THE INVENTION

The invention also relates to a method of substantially enhancing the immune system's ability to naturally eliminate or ameliorate viral and bacterial infections when the effective amount of this pharmacological composition as set forth above is taken. In addition, the invention relates to a method of substantially boosting the body's capacity to alleviate colds, the flu, sinus infections, stomach infections, joint problems, asthma, and cancer, among other conditions, when the effective amount of this composition as set forth above is taken.

The object of the invention is to develop herbal composition with different types of polyphenols (antioxidants) and Anti-inflammatories that demonstrate insulin resistance to regulate diabetes mellitus. Further object is to develop a herbal composition that reduces oxidative stress to target cardiovascular diseases.

Another object is to develop herbal composition with high antiviral & anti-microbial activity that targets viruses and bacteria to target colds and the flu and also helps to relieve a variety of skin ailments such as psoriasis and eczema.

According to a first aspect of the invention provides an herbal composition to reduce oxidative stress, comprising therapeutically effective amounts of *Moringa Oleifera* Leaf Powder, Oregano Vulgare Leaf Extract, Shilajit extract, Spirulina, Amla fruit extract, Piperine extract.

According to a second aspect of the invention provides an herbal composition to reduce oxidative stress & Inflammation, comprising therapeutically effective amounts of *Moringa Oleifera* Leaf Powder, Oregano Vulgare Leaf Extract, Shilajit extract Rosemary Leaf extract, Pomegrante Fruit Preel extract, Spirulina, Amla fruit extract, Piperine extract.

According to a third aspect of the invention provides an herbal composition to reduce oxidative stress & Inflammation, Also, to regulate blood sugar, blood cholesterol, to treat cold, cough, Psoriasis, Eczema comprising therapeutically effective amounts of *Moringa Oleifera* Leaf Powder, Oregano Vulgare Leaf Extract, Shilajit extract Rosemary Leaf extract, Pomegrante Fruit Preel extract, Spirulina, Amla fruit extract, Fenugreek Seed Extract, Curcuma longa Extract, Piperine extract

*Moringa oleifera* leaves have essential amino acids, including the sulfur-containing amino acids in higher levels than those recommended by the Food and Agriculture Organization (FAO), with patterns similar to those of soybean seeds.

Every part of *Moringa oleifera* is a storehouse of important nutrients and antinutrients. The leaves of *Moringa oleifera* are rich in minerals like calcium, potassium, zinc, magnesium, iron and copper. Vitamins like beta-carotene of vitamin A, vitamin B such as folic acid, pyridoxine and nicotinic acid, vitamin C, D and E also present in *Moringa oleifera*. Phytochemicals such as tannins, sterols, terpenoids, flavonoids, saponins, anthraquinones, alkaloids and reducing sugar present along with anti-cancerous agents like glucosinolates, isothiocyanates, glycoside compounds and glycerol-1-9-octadecanoate. Moringa leaves also have a low calorific value and can be used in the diet of the obese.

*Moringa oleifera* provides a rare combination of zeatin (a potent antioxidant), quercetin (a flavonoid known for its ability to neutralize free radicals and relieve inflammation), beta-sitosterol (a nutrient superstar that blocks cholesterol formation or build-up and is an anti-inflammatory agent for the body), caffeoylquinic acid (another powerful anti-inflammatory compound), and kaempferol (a key nutrient that promotes healthy body cellular function). All in all, enzymatically active and bioavailable *Moringa oleifera* provides 36 natural anti-inflammatory agents. Free radical damage caused by electron-seeking, highly reactive, oxidative molecules has been identified as the source of many maladies through mechanisms such as inhibition of telomerase, changes to cellular permeability and DNA damage. It has been established that *Moringa oleifera* contains 46 different antioxidants. *Moringa oleifera* are reported to be used as a hypocholesterolemic agent, and hypoglycemic agent. Hypoglycemic herbs increase insulin secretion, increase glucose uptake by tissues and inhibit glucose absorption from intestine and glycogenolysis from liver Water-soluble extract of oregano has been described to exhibit strong anti-inflammatory activity by inhibiting COX-2 secretion (Lemay, 2006). Yoshino et al. (2006) found that oregano extract exhibited anti-inflammatory activities in mouse models of stress-induced gastritis and contact hypersensitivity. Moreover, the effect of aqueous methanol extract of *Origanum vulgare* ssp. *hirtum* on soybean lipoxygenase was described, revealing a promising potential of oregano for anti-inflammatory efficacy (Koukoulitsa, 2006. The main non-volatile compounds identified were galangin, quercetin, carnosol, caffeic acid and rosmarinic acid (Kato & Shimio, 1987; Kulisic et al., 2004). Of these, carnosol and rosmarinic acid has received the majority of attention in oregano due to their high antioxidant activity as measured by ROS activity. 14 Matsuura et al. (2003) reported the isolation of two phenolic glycosides from the extract of dried leaves of oregano. The two compounds, 4'-O-β-D-glucopyranosyl-3', 4'-dihydroxybenzyl protocatechuate and 4'-O-β-D-glucopyranosyl-3',4'-dihydroxybenzyl 4-O-methylprotocatechuate, showed comparable DPPH radical scavenging activities to quercetin and rosmarinic acid. According to the USDA database, oregano is the source of the largest number of anti-inflammatory compounds.

Oregano has been found in a recent study to be significantly better than all of the 18 currently used anti-biotics in the treatment of MRSA staph infections. The strong phenol anti-oxidants destroy pathogenic bacteria, viruses and yeasts. This super herb is very rich in anti-oxidant phytochemical flavonoids and phenolic acids. It is the third highest herb in oxygen radical absorbance capacity (ORAC) with an impressive score of 200,129. Oregano is one of the world's greatest sources of the powerful phenol component thymol. Thymol is great for improving digestive function as well as destroying harmful microbes.

The USDA ranks oregano's antioxidant capacity anywhere from 3 to 20 times higher than any other herb. Oregano has four times the antioxidant power of blueberries, 12 times that of oranges and 42 times greater than apples.

Studies have shown that carvacrol, a phenol anti-oxidant within oregano has powerful anti-inflammatory and antimicrobial activity when applied to food or taken in supplement form. Oregano also contains rosmarinic acid which has very strong cancer fighting properties.

"Rosemary", also known as *Rosmarinus officinalis* has antioxidant, anti-inflammatory, and antimicrobial properties; it has been demonstrated as safe when taken in the health augmenting amount that has been set forth above. The active components of "Rosemary" include: caffeic acid derivatives (e.g., rosmarinic acid), phenolic diterpenes, flavones, and ursolic acid, which is a triterpene. Secondary compounds related to the antioxidant and antimicrobial capacity of "Rosemary" are the diterpenes carnosol and carnosic acid.

"Rosemary" has specific antimicrobial activity, or substances that target harmful microorganisms or prevent them from growing. Common microorganisms that can make people sick include *E. coli, salmonella*, and *streptococcus*, which causes strep throat and other serious infections. The carnosic acid and rosmarinic acid components of "Rosemary" have antimicrobial properties that boost the immune system's capacity to purify the blood and destroy these types of bacteria. The carnosic acid in "Rosemary" also protects the brain from oxidative damage and slows the aging of the brain.

Amla is well-known for its rich vitamin C (ascorbic acid) and polyphenol contents *Phyllanthus emblica*, also known as amla, has been used in Ayurveda, the ancient Indian system of medicine. It has been used for treatment of several disorders such as common cold, scurvy, cancer and heart diseases. It is believed that the major constituent responsible for these activities is vitamin C (ascorbic acid). Ascorbic acid shows antioxidant, anti-inflammatory and antimutagenic properties. It is a very effective free-radical scavenger. However, there are some in vivo studies indicating that antioxidant activities of amla cannot be attributed to ascorbic acid alone and that the overall effect is due to other polyphenols such as ellagic acid, gallic acid, tannins, etc. It is in fact reported that autoxidation of ascorbic acid can actually increase free-radical production. Important constituents (including gallic acid, gallotanin, ellagic acid and corilagin), possess anti-diabetic effects through their anti-oxidant and free radical scavenging properties. Amla has also been reported to prevent/reduce hyperglycemia, cardiac complications, diabetic nephropathy, neuropathy, cataract formation and protein wasting.

"Curcuma longa extract" Curcumin is the main active ingredient in *Curcuma longa* extract that has powerful anti-inflammatory properties and is a potent antioxidant. It is safely absorbed into the bloodstream, although combining it with piperine improves its absorption by about 2000%. "Curcumin" targets multiple stages of the inflammatory pathway at the molecular level. In particular, it blocks NF-kB, which is a molecule that travels into the nuclei of cells and activates genes that are associated with inflammation. Therefore, NF-kb appears to contribute to the onset of many chronic diseases and "Curcumin" blocks its activity. Furthermore, the anti-inflammatory activity of "Curcumin" is so strong that it has been reported as a safe and effective supplement that enhances the manner in which the body fights against neurodegenerative, cardiovascular, pulmonary, metabolic, autoimmune, and neoplastic diseases.

Due to the chemical structure of "Curcumin," it has the capacity to neutralize free radicals, but it also enhances the activity of antioxidant enzymes the body naturally produces "Curcumin" enhances the health of the heart by strengthening the lining of blood vessels, called the endothelium. By doing so, "Curcumin" improves the endothelium's ability to regulate blood pressure and blood clotting, and it has been shown to dramatically decrease the risk of experiencing a heart attack. In addition to boosting endothelial function, it also targets inflammatory processes and free radicals that can cause oxidative damage of the heart tissue and blood vessels.

Fennugreek seeds contain sapogenins, OH-isoleucine and galactomannans, which have been shown to exert beneficial health effects, specifically in diabetic and hypercholesterolemic animals and humans. Among the potential active components of fenugreek seeds is galactomannan, which is a guar gum representing approximately 50% of the seed weight.

Galactomannan extracted from fenugreek seeds of South Asian origin has been shown to reduce postprandial blood glucose and improve insulin sensitivity in both non-diabetic [and diabetic subjects. The decrease in postprandial blood glucose reduced the need for antidiabetic medication, including insulin, in diabetic subjects consuming diets containing guar gum. Feeding guar-Galactomannan fibre has also been shown to reduce both total and LDL cholesterol levels in healthy and type 2 diabetic (T2D) subjects.

The Pomegranate peel extract is a potent virucidal agent against genital herpes virus due to tannins. It was also used to treat the infection of male or female sexual organs. mastitis, acne, folliculitis, pile, allergic dermatitis and dysentery. Pomegranate peel and seed possessed potent antioxidant properties Polyphenols from pomegranate fermented juice, peel and seed oil and ethanolic juice were found synergistically inhibited the proliferation and induced apoptosis of human prostate cancer cells.

Research has even shown that "pomegranate peel" can disrupt the activity of a pro-inflammatory protein that is largely responsible for the development of osteoporosis, a common condition that results in brittle bones. Pro-inflammatory proteins can also lead to the breakdown of cartilage in joints, which can lead to osteoarthritis. By blocking the activity of these types of proteins, "pomegranate peel" can promote the reduction of chronic inflammation and reverse the effects of osteoporosis and osteoarthritis. The polyphenols (antioxidants) in "pomegranate peel" help maintain low cholesterol levels and safely increases blood flow throughout the entire body, which reduces the workload of the heart and protects this vital organ.

PM10 exposure is associated with the incidence and development of cardiopulmonary disease. Although the precise molecular mechanisms are yet unclear, PM10 is known to stimulate alveolar macrophages and airway epithelial cells to produce inflammatory mediators such as TNF-α and IL-1β. Particulate matter is also shown to activate endothelial cells involved in inflammation. PM10 has been shown to induce the expression of adhesion molecules and the adhesion of monocytes to human umbilical endothelial cells. The mechanism of action of PM10 may include the production of ROS and activation of NF-κB pathway, leading to inflammation. Thus, the inflammation due to PM10 is similar to sepsis in the clinical setting Pomegranate Peel extract is a well-known source of polyphenolic antioxidants and its anti-inflammatory properties have been demonstrated in various experimental models. New study in 2016 showed that Pomegranate Peel extract attenuated the PM10-induced ROS generation, expression, and secretion of TNF-α, IL-1β, MCP-1, and ICAM-1. In addition, PPE was shown to attenuate the adhesion of PM10-stimulated THP-1 cells to endothelial cells. Thus, Pomegranate Peel extract is suggested to provide health benefits by mitigating inflammatory events stimulated by particulate matter.

"Spirulina", also known as Blue-Green Algea or cyanobacterium, has potent antioxidant and anti-inflammatory properties due to its main active ingredient called phycocyanin. Phycocyanin targets oxidative damage by fighting free radicals and inhibiting the production of inflammatory substances, thereby enhancing the body's capacity to prevent the development of chronic inflammation that is associated with various diseases including cancer. "Spirulina" is also a good source of protein, copper, and vitamins B1 (Thiamin), B2 (Riboflavin), and B3 (Niacin), iron, magnesium, potassium, manganese, omega-3 fatty acids, and several others.

"Spirulina" has been shown to help lower total cholesterol, LDL (bad) cholesterol, and triglycerides, while raising HDL (good) cholesterol. The ability of "Spirulina" to improve lipid (fat) profiles also has positive implications for diabetes regulation. Lipid peroxidation, in which LDL lipoproteins in the blood become oxidized, is another major factor that is associated with increases in LDL cholesterol and subsequent diseases. The high antioxidant content of "Spirulina" safely disrupts lipid peroxidation, while enhancing the levels of antioxidant enzymes in the blood. Therefore, "Spirulina" boosts the immune system's ability to reduce markers of oxidative damage. Furthermore, it boosts hemoglobin content in red blood cells as well as immune system function, which reduces anemia, feelings of weakness, and fatigue. Its high antioxidant content detoxifies the body, enhances physical performance, muscle strength, and endurance, but also increases the time it takes to become fatigued by minimizing exercise-induced oxidative damage.

"Shilajit", also known as Asphaltum, is a rare, but potent, substance that has been shown to safely boost the immune system and promote detoxification. Shilajit contains over 85 minerals that have strong energy-enhancing effects, as well as selenium, humic acid, dibenzo-α-pyrones, and fulvic acid. The selenium in "Shilajit" has antioxidant properties that protect cells from unnecessary damage, enhance energy, and help prevent various diseases. Its humic acid component binds to harmful metals that enter certain farm-grown plants and promotes metal detoxification. This helps restore the body's natural balance and also prevents illness. Fulvic acid has potent anti-aging activity and research has shown that the more fulvic acid a substance contains the greater its anti-aging ability. Shilajit contains between 60 to 80% fulvic acid. Researchers have demonstrated that shilajit shows potent antioxidant properties. While it isn't actually an antioxidant itself, it mimics extremely powerful antioxidants found in nature. Shilajit promotes cellular respiration (that would usually cause oxidation), but it has also been shown to decrease oxidation rate and prevent damage caused by oxidation while inhibiting ongoing lipid peroxidation. Processed shilajit extract has also been shown to trap hydroxyl radicals, NO- and SO-radicals as well as regenerate ascorbic acid. In a 1996 study, shilajit was used in a herbal formulation on animals with induced diabetes. The scientists were able to demonstrate that the formulation can be successful in treating diabetes through the regeneration and repair of the endocrine pancreas. (S. K. Mitra 1996). A similar study demonstrated shilajit combined with pharmaceuticals in two of three doses each case helped the lipid profile and showed a notable reduction of blood glucose in diabetic rats. (N. A. Trivedi 2004)

"Piperine", also referred to as *Piper nigrum*, and most commonly known as black pepper is a highly potent mineral that helps boost the absorption of other nutrients and is well-known for safely supporting the reduction of muscular pain, joint pain, and even the symptoms of bronchitis, heart disease, and Parkinson's by specifically targeting inflammatory and plaque-reduction processes. One of the biggest benefits of "Piperine", however, is its ability to safely increase the availability of additional nutrients that the body needs. For example, levels of vitamin B6, C, and even selenium dramatically increase when *piper nigrum* is consumed regularly. "Piperine" also aids the absorption of nutrients in the bloodstream and gastrointestinal tract, which boosts metabolism. An increased metabolic rate has the ability to help individuals safely lose weight.

TABLE

| Ingredients | Weight in mg |
|---|---|
| Orally Administered Herbal Composition 1 Formulation Per Serving (4-6 Capsules ) | |
| Moringa Oleifera Leaf Powder | 150 mg |
| Oregano Leaf Extract (Polyphenols) | 80 mg |
| Shilajit (Fulvic Acid) | 40 mg |
| Spirulina | 40 mg |
| Amla Fruit Extract(Polyphenols) | 50 mg |
| Piperine extract | 2 mg |
| Orally Administered Herbal Composition 2 Formulation Per Serving (4-6 Capsules ) | |
| Moringa Oleifera Leaf Powder | 100 mg |
| Oregano Leaf Extract (Polyphenols) | 50 mg |
| Rosemary Extract (Rosmarinic acid) | 40 mg |
| Shilajit (Fulvic Acid) | 40 mg |
| Pomegranate Peel Extract (Polyphenols) | 40 mg |
| Spirulina | 40 mg |
| Amla Fruit Extract(Polyphenols) | 50 mg |
| Piperine extract | 2 mg |
| Orally Administered Herbal Composition 3 Formulation Per Serving (4-6 Capsules ) | |
| Moringa Oleifera Leaf Powder | 100 mg |
| Oregano Leaf Extract (Polyphenols) | 30 mg |
| Rosemary Extract (Rosmarinic acid) | 30 mg |
| Shilajit (Fulvic Acid) | 40 mg |
| Pomegranate Peel Extract (Polyphenols) | 30 mg |
| Fenugreek Seed Extract(Galactomanan) | 60 mg |
| Curcuma longa Extract (Curcumin) | 10 mg |
| Spirulina | 40 mg |
| Amla Fruit Extract (Polyphenols) | 40 mg |
| Piperine extract | 2 mg |

The HPMC capsules containing the composition set forth in the table above may composed of magenesium stearate, silicon di oxide, rice flour. For oral administration of the above-recited herbal compositions, 4-6 capsules daily one serving in empty stomach with plenty of warm water

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

Figure 1A:
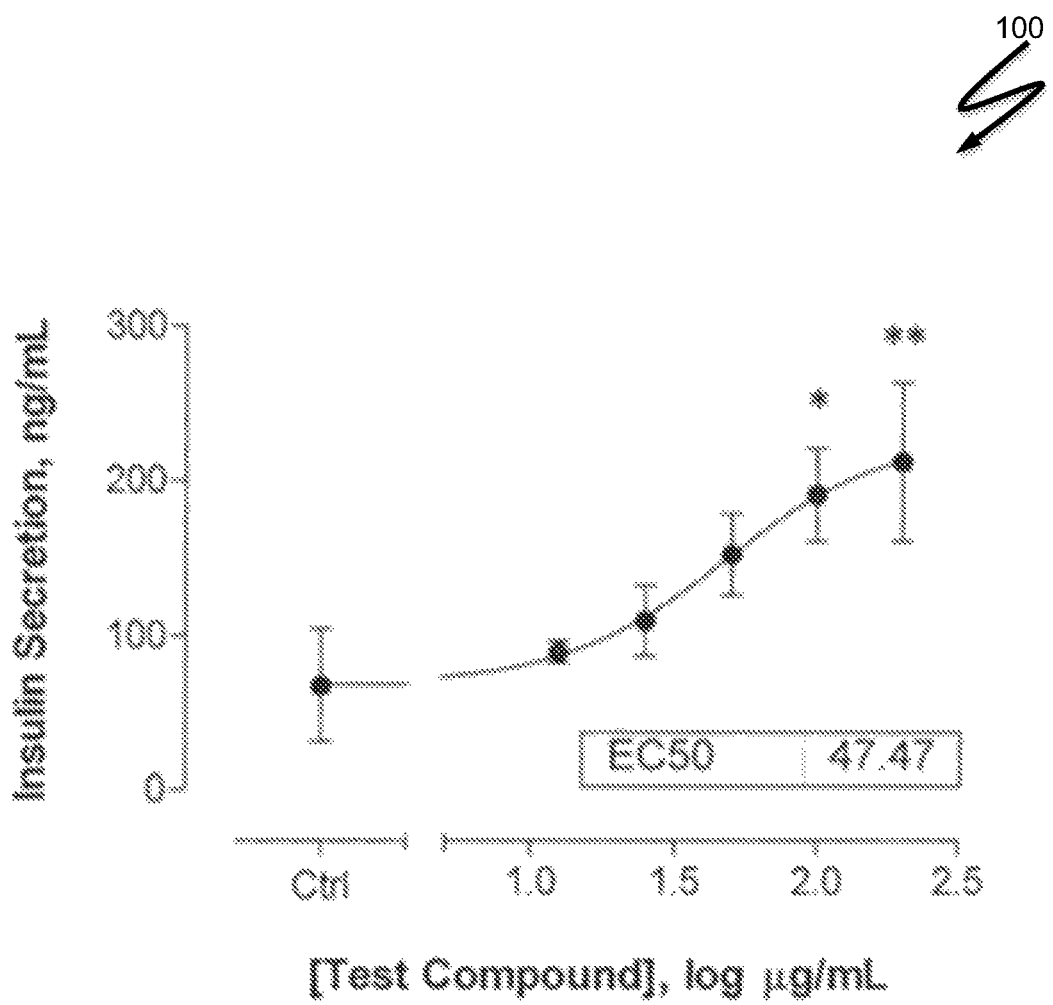
FIG. 1A illustrates a graph illustrating increase in insulin secretion by the present herbal supplement composition 3, in accordance with one embodiment of the present invention.

While the present systems and methods have been described herein by way of example for several embodiments and illustrative drawings, those skilled in the art will recognize that the multiple embodiments disclosed hereinbelow are not limited to the embodiments or drawings described. It should be understood, that the drawings and detailed description thereto are not intended to limit embodiments to the particular form disclosed. Rather, the intention is to cover all modifications, equivalents and alternatives falling within the spirit and scope of the invention as defined by the appended claims. Any headings used herein are for organizational purposes only and are not meant to limit the scope of the description or the claims. As used herein, the word "can" and "may" is used in a permissive sense (i.e., meaning having the potential to), rather than the mandatory sense (i.e., meaning must). Similarly, the words "include", "including", and "includes" mean including, but not limited to.

DETAILED DESCRIPTION

Experimental Data

Experiment 1: To Evaluate ORAC (Oxygen Radical Absorbance Capacity) of Herbal Supplement Composition 1

The Objective of the experiment is to Evaluate ORAC (Oxygen Radical Absorbance Capacity) of Herbal Supplement composition. Oxygen Radical Absorbance Capacity (ORAC) tests are among the most acknowledged methods that measure antioxidant scavenging activity against oxygen radicals that are known to be involved in the pathogenesis of aging and many common diseases. ORAC 5.0 consists of five types of ORAC assays that evaluate the antioxidant capacity of a material against six primary reactive oxygen species (ROSs, commonly called "oxygen radicals") found in humans: peroxyl radical, hydroxyl radical, superoxide anion, singlet oxygen. This is a comprehensive panel that evaluates the antioxidant capacity of a material against oxygen radicals The ORAC tests are based on evaluating the capacity of an interested material to protect a probe (a fluorescent probe or chromagen) from its damage by ROSs. In all ORAC assays, an ROS inducer is introduced to the assay system. The ROS inducer triggers the release of a specific ROS, which would degrade the probe and cause its emission wavelength or intensity change. When an antioxidant material presents in the environment, the antioxidant absorbs the ROS and preserves the probe from degradation. The degree of probe preservation indicates the antioxidant capacity of the material. Trolox is used as the reference standard, and the results are expressed as µmole Trolox equivalency per gram (or milliliter) of a tested material.

TABLE 1

ORAC Score (Oxygen Radical Absorbance Capacity) of Herbal Supplement composition 1 against free radicals

| Radicals | Result |
|---|---|
| ORAC against peroxyl radicals | 5,219 µmole TE/serving size |
| ORAC against hydroxyl radicals | 10,964 µmole TE/serving size |
| ORAC against peroxynitrite | 543 µmole TE/serving size |
| ORAC against super oxide anion | 6,152 µmole TE/serving size |
| ORAC against singlet oxygen | 1,244 µmole TE/serving size |

There are six predominant reactive species found in the body: peroxyl radicals, hydroxyl radicals, peroxynitrite, super oxide anion, singlet oxygen and hypochlorite. ORAC 5.0 provides a measure of the total antioxidant power of a food/nutrition product against the six predominant reactive species. The ORAC result is expressed as micromole Trolox equivalency (µmole TE) per gram. Serving size=2.17 g Experiment 2: To Evaluate Effect of Herbal Supplement Composition 2 on 2,2-Diphenyl-1-picrylhydrazyl (DPPH) Radical Scavenging Activity Briefly, 12.5 mg of the herbal composition 2 contents was weighed, dissolved in 312.5 µl of DMSO and the volume was made up to 10 ml with 100% methanol. Further dilutions were done in 100% methanol containing 3.125% of DMSO. The sample was found to be approximately 70% soluble upon visual inspection. For calculation purposes the sample was considered to be 100% soluble.

Gallic acid (reference inhibitor) preparation. For gallic acid, a stock of 200 µg/ml was prepared by dissolving 2 mg of gallic acid in 10 ml of methanol. Further dilutions were made as required with methanol. The sample was found to be approximately 100% soluble upon visual inspection.

DPPH assay was carried out as per the method of Vani et al [4]. In brief, the total reaction mixture contained methanol/vehicle buffer/positive control/various concentrations of test solution and DPPH to a final concentration of 0.132 mM. The reaction mixture was incubated at 25° C. for 20 minutes. Following incubation the absorbance was read at 510 nm using a micro-well plate reader (Molecular devices Versamax microplate reader). A control reaction was carried out without test samples.

The % inhibition values were calculated as follows:

$$\% \text{ inhibition} = \frac{\text{Absorbance(control)} - \text{Absorbance(test)}}{\text{Absorbance(control)}} \times 100$$

Where, Absorbance=Final Absorbance−Initial absorbance. $IC_{50}$ was calculated using log-probit analysis.

Herbal composition 2 exhibited DPPH free radical scavenging activity in a dose dependent manner in the concentration range tested.

Herbal composition 2 exhibited an $IC_{50}$ of 50.70 µg/ml in DPPH free radical scavenging assay

TABLE 02

$IC_{50}$ data of Herbal composition 2 and reference inhibitor in DPPH radical scavenging assay

| Sample | Concentration (µg/ml) | % Inhibition (Mean ± SEM) | $IC_{50}$ (µg/ml) (95% Confidence Interval) |
|---|---|---|---|
| Gallic Acid (Reference Inhibitor) | 0.5 | 8.71 ± 1.12 | 2.09 |
| | 1.5 | 32.14 ± 2.42 | (1.81-2.42) |
| | 2.5 | 60.58 ± 2.84 | |
| | 5 | 80.52 ± 0.57 | |
| Herbal composition 2 | 5 | 9.89 ± 5.79 | 50.70 |
| | 10 | 13.59 ± 3.71 | (42.84-59.81) |
| | 25 | 23.76 ± 1.56 | |
| | 50 | 41.36 ± 2.70 | |
| | 100 | 75.05 ± 3.22 | |
| | 250 | 93.13 ± 0.64 | |
| | 500 | 94.04 ± 0.78 | |
| | 1000 | 94.28 ± 0.54 | |

Experiment 3: To Evaluate the Effect of Herbal Supplement Composition 2 on LDL Oxidation in a Cell-Free System Briefly, 29.73 mg of the Herbal composition 2 contents was weighed, dissolved in 500 µl of DMSO and the volume was made up to 25 ml with phosphate buffered saline. The sample was found to be approximately 70% soluble upon visual inspection. The sample was filtered and the filtrate was used for the assay. For calculation purposes the sample was considered to be 100% soluble.

Trolox (reference inhibitor) preparation, For trolox, a stock of 8 mM was prepared by dissolving 2 mg of trolox in 2 ml of phosphate buffered saline. The sample was found to be approximately 100% soluble upon visual inspection. Further dilutions were made as required with phosphate buffered saline.

The assay was carried out as per the method of Hodgson et al [3] with modifications. In brief, the reaction mixture contained phosphate buffered saline/vehicle buffer/positive control/test sample of various concentrations and serum from fasting human. Copper sulphate solution was added to the reaction mixture to start the reaction. The reaction mix was mixed and read immediately at 234 nm using a UV-VIS spectrophotometer, for the initial reading, and incubated. After the completion of incubation period, the final absorbance was measured at 234 nm. A control reaction was carried out without test samples.

The % inhibition values were calculated as follows:

$$\% \text{ inhibition} = \frac{\text{Absorbance(control)} - \text{Absorbance(test)}}{\text{Absorbance(control)}} \times 100$$

Where, Absorbance=Final Absorbance−Initial absorbance. $IC_{50}$ was calculated using log-probit analysis.

Herbal composition 2 was tested in LDL oxidation inhibition assay at concentrations ranging from 37.03 µg/ml to 1000 µg/ml. The sample exhibited inhibition of LDL oxidation in a dose dependent manner in the concentration range tested. The $IC_{50}$ of Herbal composition in LDL oxidation inhibition assay was found to be 77.75 µg/ml.

TABLE 03

IC$_{50}$ data of positive control and test herbal composition 2 in LDL oxidation inhibition assay

| Sample | Concentration | % Inhibition (Mean ± SEM) | IC$_{50}$ (95% Confidence Interval) |
|---|---|---|---|
| Trolox (Reference Inhibitor) | 0.25 µM | 48.80 ± 6.21 | 0.18 µM |
| | 0.5 µM | 73.07 ± 3.39 | (0.06-0.29) |
| | 1.0 µM | 76.33 ± 0.07 | |
| | 2.0 µM | 79.04 ± 0.64 | |
| Herbal Composition 2 | 37.03 µg/ml | 43.11 ± 12.62 | 77.75 µg/ml |
| | 111.11 µg/ml | 45.93 ± 0.09 | (57.09-99.95) |
| | 333.33 µg/ml | 75.23 ± 0.59 | |
| | 1000 µg/ml | 100.00 ± 0.00 | |

Experiment 4: To Evaluate the Effect of Herbal Supplement Composition 2 on Super Oxide Radical Scavenging Activity Briefly, 8 mg of the Herbal composition 2 contents was weighed, dissolved in 200 µl of DMSO and the volume was made up to 2 ml with 0.1M phosphate buffer pH 7.4. Further dilutions were done in 0.1M phosphate buffer pH 7.4 containing 10% of DMSO. The sample was found to be approximately 70% soluble upon visual inspection. For calculation purposes the sample was considered to be 100% soluble.

Gallic acid (reference inhibitor) preparation, For gallic acid, a stock of 500 µg/ml was prepared by dissolving 5 mg of gallic acid in 10 ml of 0.1M phosphate buffer pH 7.4. The sample was found to be approximately 100% soluble upon visual inspection. The assay was carried out as per the method of Yen et al. [5] with modifications. In brief, the reaction mixture contained 0.1M phosphate buffer pH 7.4/ vehicle buffer/positive control/test sample of various concentrations, 292.5 µM NADH, 37.5 µM NBT and 15 µM PMS. The plate was mixed and incubated at 25° C. for 5 minutes. The absorbance was measured at 560 nm in a micro-plate reader (Versamax, Molecular devices). A control reaction was carried out without test samples.

The % inhibition values were calculated as follows:

$$\% \text{ inhibition} = \frac{\text{Absorbance(control)} - \text{Absorbance(test)}}{\text{Absorbance(control)}} \times 100$$

IC$_{50}$ was calculated using log-probit analysis.

Herbal composition 2 was tested in super oxide radical scavenging assay at concentrations ranging from 5 µg/ml to 1000 µg/ml. The sample exhibited scavenging of super oxide radicals activity in a dose dependent manner in the concentration range tested. The IC$_{50}$ of Herbal composition 2 in super oxide radical scavenging assay was found to be 68.37 µg/ml.

TABLE 04

IC$_{50}$ data of positive control and test herbal composition 2 in super oxide radical scavenging assay

| Sample | Concentration (µg/ml) | % Inhibition (Mean ± SEM) | IC$_{50}$ (µg/ml) (95% Confidence Interval) |
|---|---|---|---|
| Gallic acid (Reference Inhibitor) | 5 | 27.00 ± 3.37 | 17.86 |
| | 10 | 32.89 ± 3.26 | (14.53-21.76) |
| | 20 | 47.80 ± 4.26 | |
| | 40 | 69.50 ± 1.00 | |
| | 80 | 83.67 ± 0.00 | |
| Herbal Composition 2 | 5 | 4.09 ± 1.72 | 68.37 |
| | 10 | 7.33 ± 2.63 | (57.45-81.33) |
| | 25 | 28.33 ± 1.71 | |
| | 50 | 52.50 ± 1.11 | |
| | 100 | 62.37 ± 0.63 | |
| | 250 | 75.19 ± 0.14 | |
| | 500 | 87.24 ± 0.37 | |
| | 1000 | 93.66 ± 2.26 | |

Experiment 4: To Evaluate ORAC(Oxygen Radical Absorbance Capacity) of Herbal Supplement Composition 1

The Objective of the experiment is to Evaluate ORAC (Oxygen Radical Absorbance Capacity) of Herbal Supplement composition. Oxygen Radical Absorbance Capacity (ORAC) tests are among the most acknowledged methods that measure antioxidant scavenging activity against oxygen radicals that are known to be involved in the pathogenesis of aging and many common diseases. ORAC 5.0 consists of five types of ORAC assays that evaluate the antioxidant capacity of a material against six primary reactive oxygen species (ROSs, commonly called "oxygen radicals") found in humans: peroxyl radical, hydroxyl radical, superoxide anion, singlet oxygen, peroxynitrite and hypochlorite. This is a comprehensive panel that evaluates the antioxidant capacity of a material against oxygen radicals The ORAC tests are based on evaluating the capacity of an interested material to protect a probe (a fluorescent probe or chromagen) from its damage by ROSs. In all ORAC assays, an ROS inducer is introduced to the assay system. The ROS inducer triggers the release of a specific ROS, which would degrade the probe and cause its emission wavelength or intensity change. When an antioxidant material presents in the environment, the antioxidant absorbs the ROS and preserves the probe from degradation. The degree of probe preservation indicates the antioxidant capacity of the material. Trolox is used as the reference standard, and the results are expressed as µmole Trolox equivalency per gram (or milliliter) of a tested material.

TABLE 5

ORAC Score (Oxygen Radical Absorbance Capacity) of Herbal Supplement composition 1 against free radicals

| Radicals | Result |
|---|---|
| ORAC against peroxyl radicals | 3,857 µmole TE/serving size |
| ORAC against hydroxyl radicals | 10,860 µmole TE/serving size |
| ORAC against peroxynitrite | 480 µmole TE/serving size |
| ORAC against super oxide anion | 3,924 µmole TE/serving size |
| ORAC against singlet oxygen | 392 µmole TE/serving size |

Experiment 5: Effect of Herbal Supplement Composition 3 on Insulin Release in Rat Islets The objective of the experiment is to evaluate the effect of herbal supplement test composition on insulin secretion in rat pancreatic islets. Insulin, a peptide hormone, is secreted by pancreatic β-cells and is a key regulator in glucose homeostasis. Insulin deficiency leads to insulin-dependent (type 1) diabetes, whereas resistance to insulin action is common in non-insulin-dependent diabetes (type 2), obesity, and endocrine dysfunctions. The pancreatic β-cells are known to be sensitive to the glucose concentration in the blood. When the blood glucose levels are high they secrete insulin into the blood; when the levels are low they cease their secretion of this hormone into the general circulation. Insulin released by the β-cells is the main regulator of glucose levels. Stimulation of insulin release from β-cells is one of the major mechanisms by which natural products exhibit an anti-diabetic effect.

Firstly, the herbal supplement composition is dissolved in DMSO with sonication for 15 min and centrifuged at 10,000 rpm for 10 minutes at room temperature to remove insoluble debris. Glyburide (CAS: 10238-21-8) and Glucose are used as reference compounds in the present experiment. Glyburide (CAS: 10238-21-8) is dissolved in DMSO and used at 3 μM. Glucose is dissolved in water and used at 2.5 mM and 11.5 mM as a control. The rat pancreatic islets are isolated using standard in-house procedures. After culturing overnight, islets are starved in starvation media (KRBH buffer containing 0.01% BSA, no glucose) for about 1 hr. After starvation, islets are selected and added to 20 μl of KRBH buffer containing 0.01% BSA to each well of a 96 well plate (4 islets/well). The supplement composition is then added to each well at the indicated concentrations. Glucose is also added to control wells at a concentration of 2.5 mM for no insulin secretion and 11.5 mM for maximum glucose-stimulated insulin secretion, and the plate is incubated for 1 hr at 37° C. at 5% $CO_2$.

At the end of the 1 hr incubation period, 20 μl of supernatant is gently transferred to another plate. Insulin secretion is measured using the Mercodia Rat Insulin ELISA kit according to the manufacturer's protocol. The DMSO concentration in the assay is maintained at less than equal to 1.0%. The data is fit to a non-linear regression using Graph pad Prism (version 5.0). The half maximal effective concentration ($EC_{50}$) is obtained from the sigmoidal dose response and variable slope curve is generated. Statistical analyses are carried out using a one-way ANOVA followed by a Dunnett's multiple comparison test. The data represents five replicates for each condition.

Figure 1B:
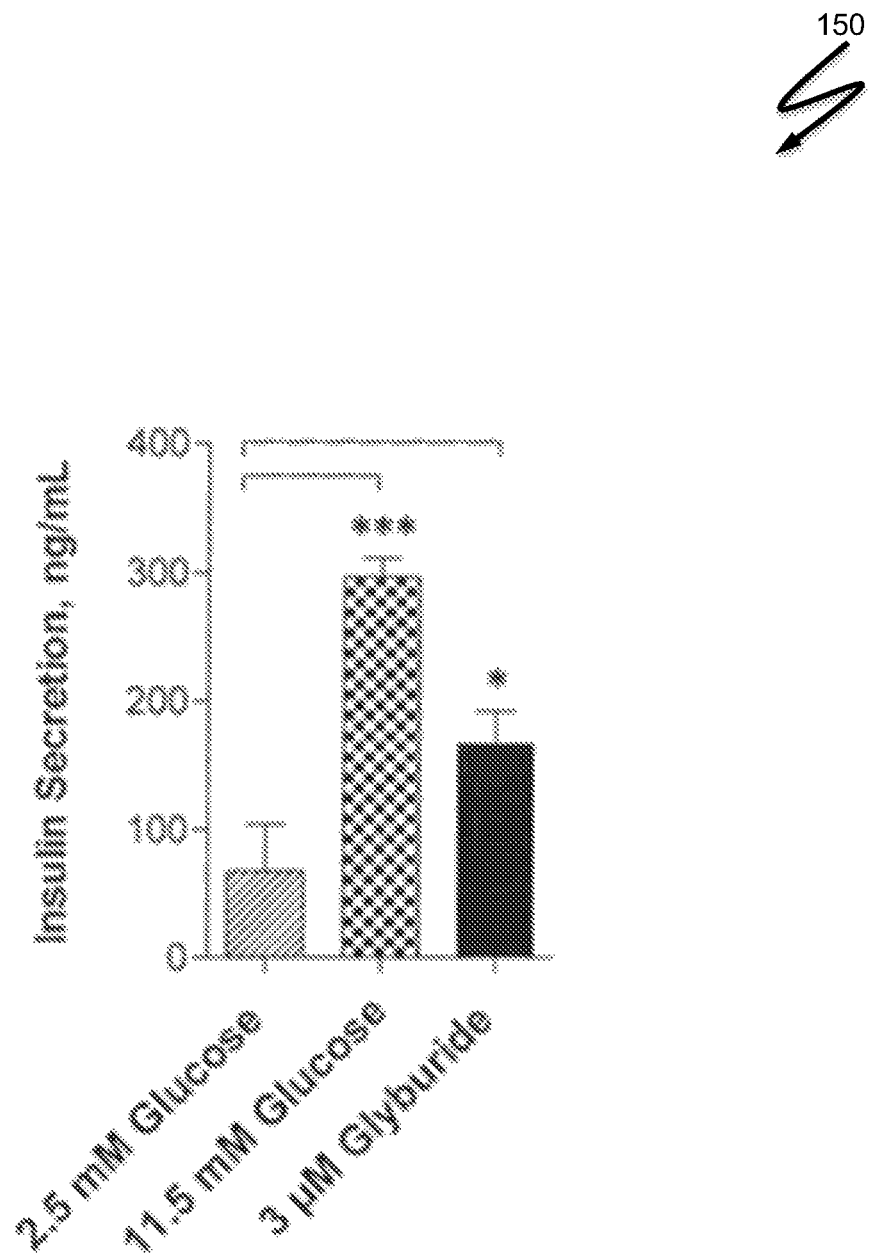
FIG. 1B illustrates a graph illustrating increase in insulin secretion by glyburide and glucose, by present herbal composition 3 in accordance with one embodiment of the present invention.

FIG. 1A illustrates a graph 100 illustrating increase in insulin secretion by the present herbal Supplement composition, in accordance with one embodiment of the present invention. FIG. 1B illustrates a graph 150 illustrating increase in insulin secretion by glyburide and glucose, in accordance with one embodiment of the present invention. The supplement composition significantly increases insulin secretion in rat pancreatic islets in a dose-dependent manner with an $EC_{50}$ of 47 μg/mL as illustrated in FIG. 1A of the present invention. However, a significant increase in insulin secretion is also observed with 3 μM Glyburide and 11.5 mM glucose. The error bars in FIG. 1A and FIG. 1B represent Mean±SEM (Standard Error of the Mean) where, *P<0.001, P<0.01, *P<0.05, and one-way ANOVA is followed by Dunnett's test. Table 1 below provides data related to Insulin secretion (ng/ml) as a function of supplement composition concentration.

TABLE 6

Insulin secretion (ng/ml) as a function of supplement composition 3 concentration

| Supplement Composition, μg/ml | Insulin Secretion, ng/ml (Mean ± SEM) |
|---|---|
| 0 | 67.41 ± 36.77 |
| 12.5 | 89.43 ± 6.97 |
| 25 | 109.57 ± 22.67 |
| 50 | 152.31 ± 26.4 |
| 100 | 190.67 ± 30.03 |
| 200 | 211.89 ± 51.15 |

Experiment 6: To Evaluate Effect of Herbal Supplement Composition 3 on Cholesterol Uptake in Caco-2 Cells (Human Epithelial Colorectal Adenocarcinomacells)

The objective of the experiment is to evaluate the effect of the supplement composition on cholesterol uptake in Caco-2 (human epithelial colorectal adenocarcinoma) cells. Cholesterol is both an important structural component of cell membranes and an early intermediate in hormone and bile acid biosynthesis. The supplement composition is dissolved in Dimethyl Sulphoxide (DMSO) with sonication for 15 min and centrifuged at 10,000 rpm for 10 min at room temperature to remove insoluble debris. The reference compound used in the present experiment is U-18666A (CAS: 3039-71-2), which increases cholesterol uptake by inhibiting trafficking of synthesized cholesterol. The U-18666A is dissolved in DMSO and used at a concentration of about 1.25, 2.5, 5 and 10 μM. Moreover, U-18666A is used as a positive control. The reagent used is 3-hexanoyl-NBD Cholesterol. Caco-2 cells are maintained at 60-70% confluence in complete growth medium EMEM containing 20% FBS and required antibiotic. For the assay, cells are harvested using 0.25% trypsin EDTA. The trypsinized cells are centrifuged at 1200 rpm for 5 minutes and re-suspended in growth medium. Cells are seeded at a density of 10,000 cells per well in complete growth medium (EMEM+20% FBS+ antibiotic) in poly D-lysine coated black plates, and incubated overnight at 37° C. in 5% $CO_2$. After incubation, the plates are washed with Phosphate Buffered Saline (PBS) and incubated with 20 μg/ml NBD cholesterol in the presence of the test supplement composition and positive control U-18666A in PBS at pH 7.2. The cells are incubated for 48 hrs at 37° C. in 5% $CO_2$. At the end of the incubation period, the plates are washed twice with PBS and cholesterol uptake is calculated by measuring NBD cholesterol fluorescence (Ex 485 nm, Em 535 nm). Cell viability studies are carried out using an XTT kit with varying concentration of supplement composition using the manufacturer's recommended protocol.

The DMSO concentration in the assay is maintained at less than equal to 1.0%. The data is fit to a non-linear regression using Graph pad Prism (version 5.0). The half maximal effective concentration ($EC_{50}$) is obtained from the sigmoidal dose response and variable slope curve is generated. Statistical analyses are carried out using a one-way ANOVA followed by a Dunnett's multiple comparison test. The data represent five replicates for each condition.

Figure 2A:
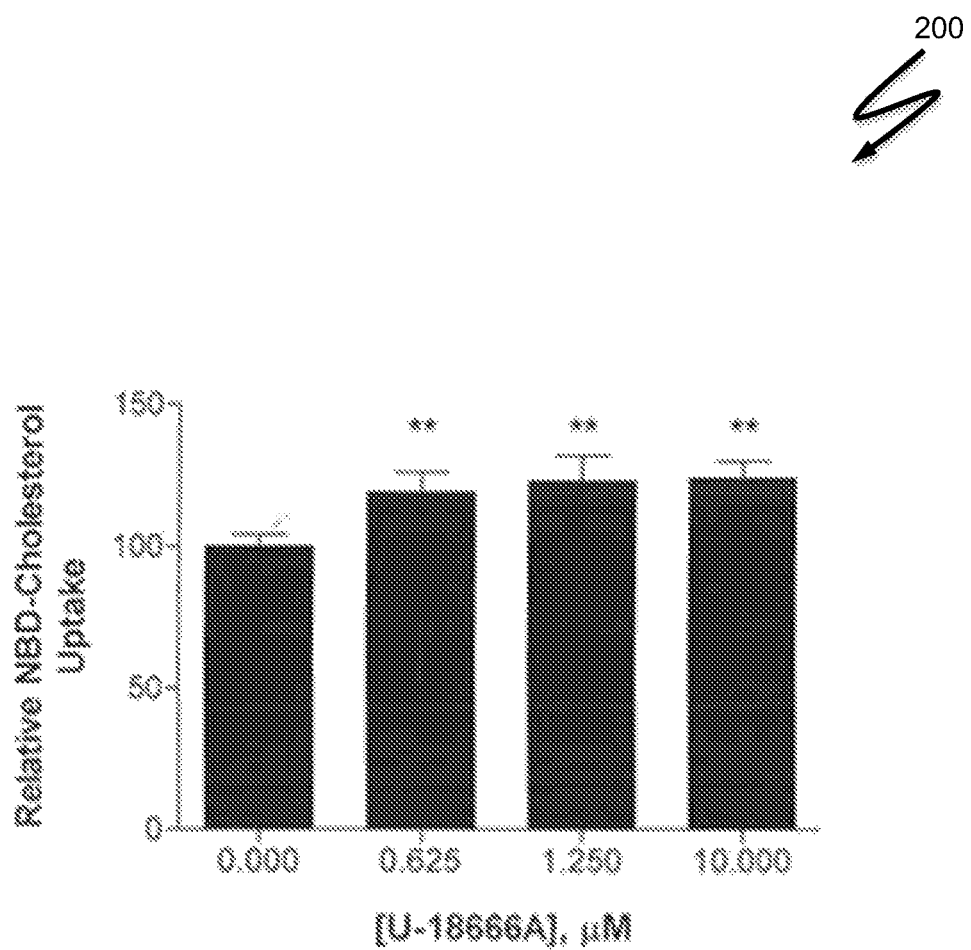
FIG. 2A illustrates a graph illustrating increase in NBD-cholesterol uptake with U-18666A, by the present herbal supplement composition 3 in accordance with one embodiment of the present invention.

FIG. 2A illustrates a graph 200 illustrating increase in NBD-cholesterol uptake with U-18666A, in accordance with one embodiment of the present invention. The results illustrate positive control standard U-18666A increased NBD-cholesterol uptake by up to 25% in Caco-2 cells. FIG.

2B illustrates a graph 250 illustrating inhibition of NBD-cholesterol uptake with the supplement composition, in accordance with one embodiment of the present invention. Particularly, the supplement composition significantly inhibited NBD-cholesterol uptake into Caco-2 cells in a dose-dependent manner.

Figure 2B:
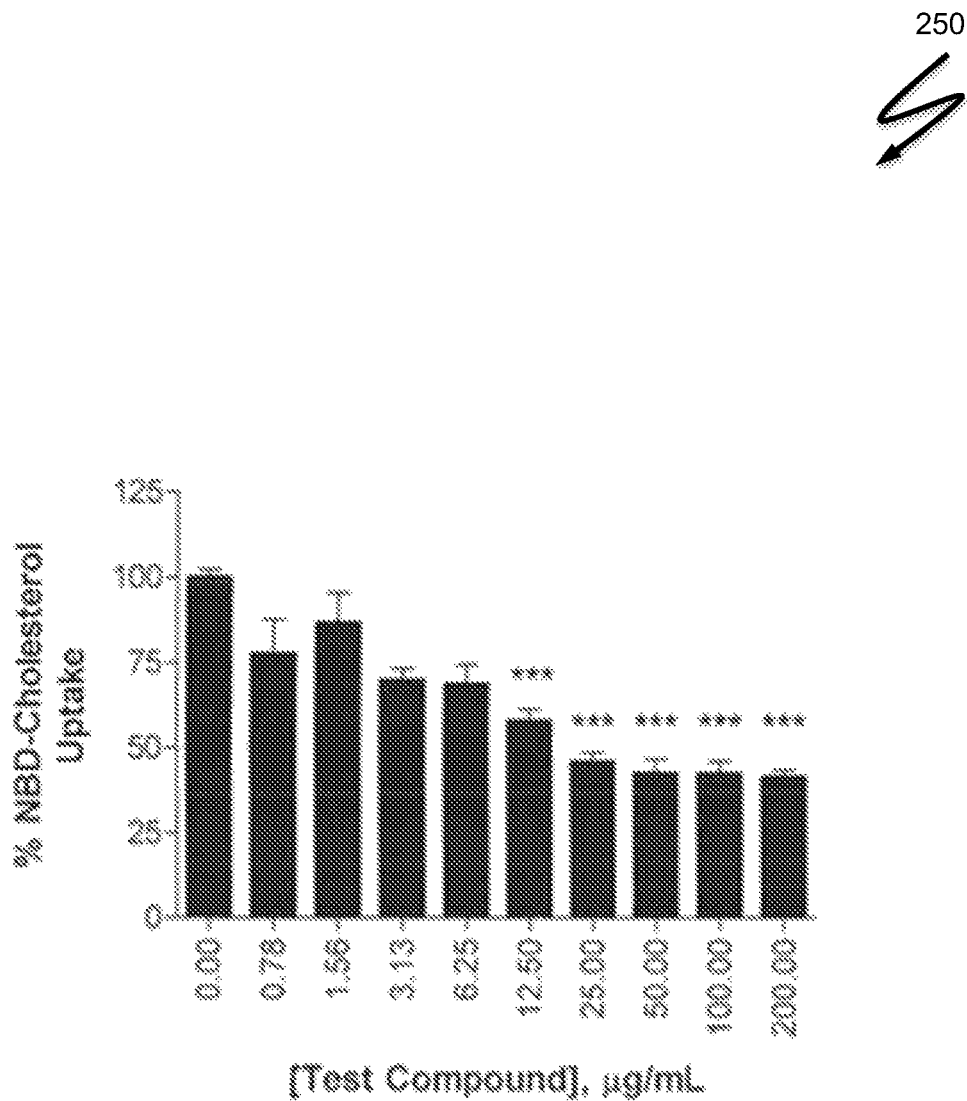
FIG. 2B illustrates a graph illustrating inhibition of NBD-cholesterol uptake with the herbal supplement composition 3, in accordance with one embodiment of the present invention.
Figure 2C:
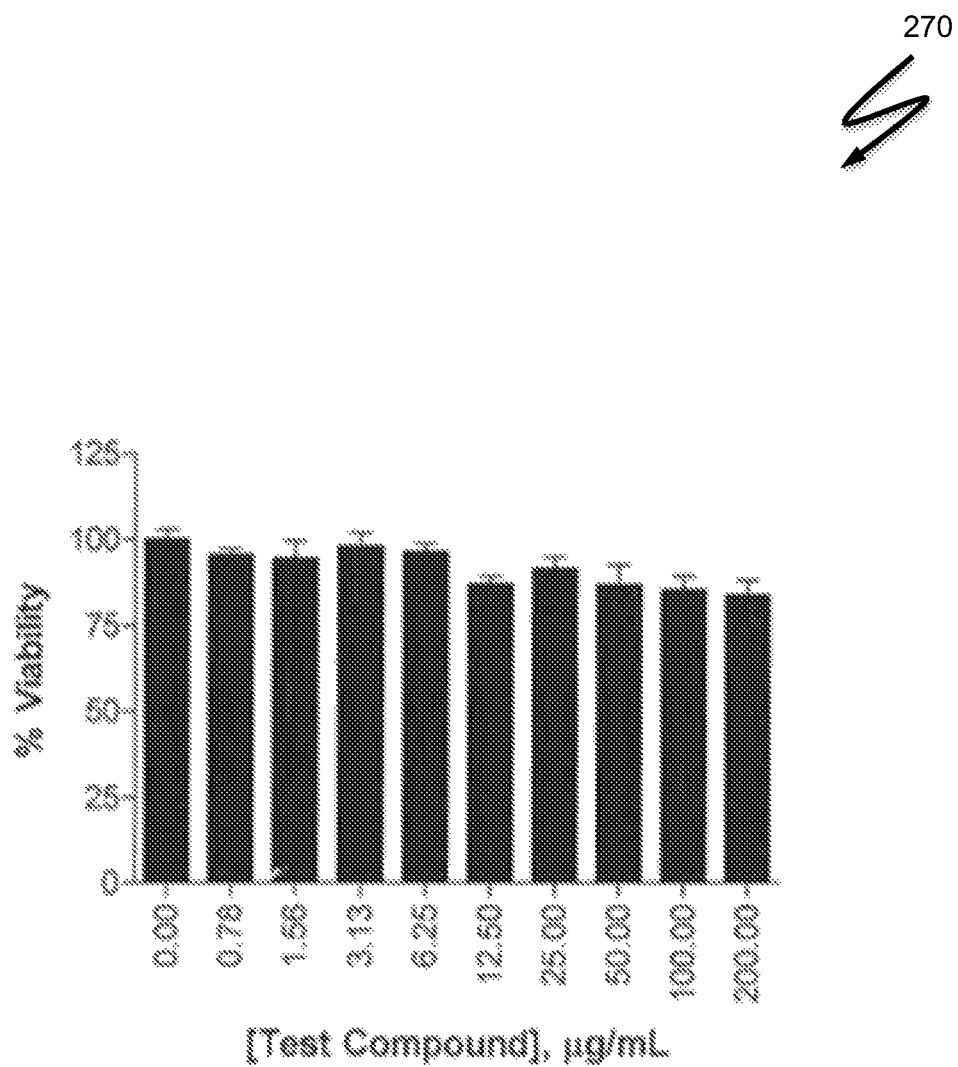
FIG. 2C illustrates a graph illustrating effect of herbal supplement composition 3 on the viability of Caco-2 cells, in accordance with one embodiment of the present invention.

FIG. 2C illustrates a graph 270 illustrating effect of supplement composition on the viability of Caco-2 cells, in accordance with one embodiment of the present invention. The decrease in NBD-cholesterol uptake is not a function of the effect of the test compound supplement composition on cell viability, as no effects are observed in the XTT assay up to 200 µg/mL. The Error bars in FIG. 2A, FIG. 2B, & FIG. 2C represent Mean±SEM where, *P<0.001, P<0.01, *P<0.05, and one-way ANOVA followed by Dunnett's test. Table 2 below illustrates data related to cholesterol uptake (% activity) as a function of supplement concentration.

TABLE 7

Cholesterol uptake (% activity) as a function of Herbal supplement composition 3.

| Supplement Composition, µg/mL | % Activity (Mean ± SEM) |
|---|---|
| 0 | 100 ± 2.35 |
| 0.78 | 77.67 ± 9.94 |
| 1.56 | 86.86 ± 8.65 |
| 3.13 | 69.84 ± 3.44 |
| 6.25 | 68.65 ± 5.75 |
| 12.5 | 57.82 ± 3.46 |
| 25 | 46.02 ± 2.55 |
| 50 | 42.51 ± 4.22 |
| 100 | 42.45 ± 3.67 |
| 200 | 41.36 ± 2.13 |

Experiment 7: To Evaluate Effect of Herbal Supplement Composition 3 on 2,2-Diphenyl-1-picrylhydrazyl (DPPH) Radical Scavenging Activity The objective of this experiment is to evaluate the effect of the supplement concentration on DPPH radical scavenging activity in a cell-free assay. The supplement concentration is dissolved in DMSO with sonication for 15 min and centrifuged at 10,000 rpm for 10 min at room temperature to remove insoluble debris. 2,2-Diphenyl-1-picrylhydrazyl (DPPH) is used as a reagent for this experiment. DPPH is an antioxidant reagent that is used as a free radical trap or scavenger. The color of DPPH changes from red to yellow as its scavenging activity increases. This is measured by absorbance at 517 nm. The reference compound used is Trolox (CAS: 53188-07-1). The Trolox is dissolved in DMSO and used at different concentrations. Trolox is used as positive control.

A reaction mix is made in 200 µL methanol containing 200 µM of DPPH and various concentrations of the supplement. The mixture is mixed gently with a pipette and left to stand for 30 min in the dark, after which absorbance readings are taken at 517 nm. The change in DPPH absorbance is calculated relative to the absorbance of DPPH alone i.e. without the supplement. The DMSO concentration in the assay is maintained at less than equal to 1.0%. The data is fit to a non-linear regression using Graph pad Prism (version 5.0). The half maximal effective concentration ($EC_{50}$) is obtained from the sigmoidal dose response and a vertical slope curve is generated. The data represent three replicates for each condition.

Figure 3A:
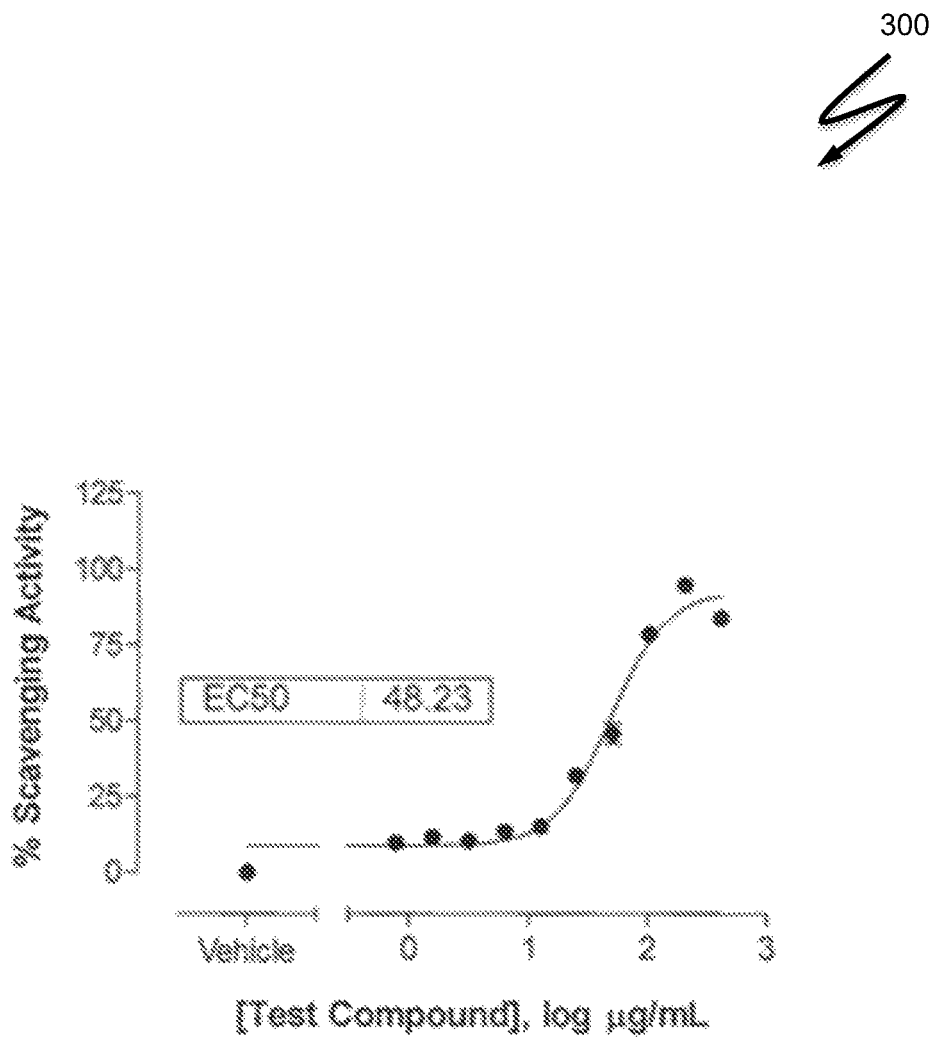
FIG. 3A illustrates a graph illustrating DPPH radical scavenging activity by the herbal supplement composition 3, in accordance with one embodiment of the present invention.
Figure 3B:
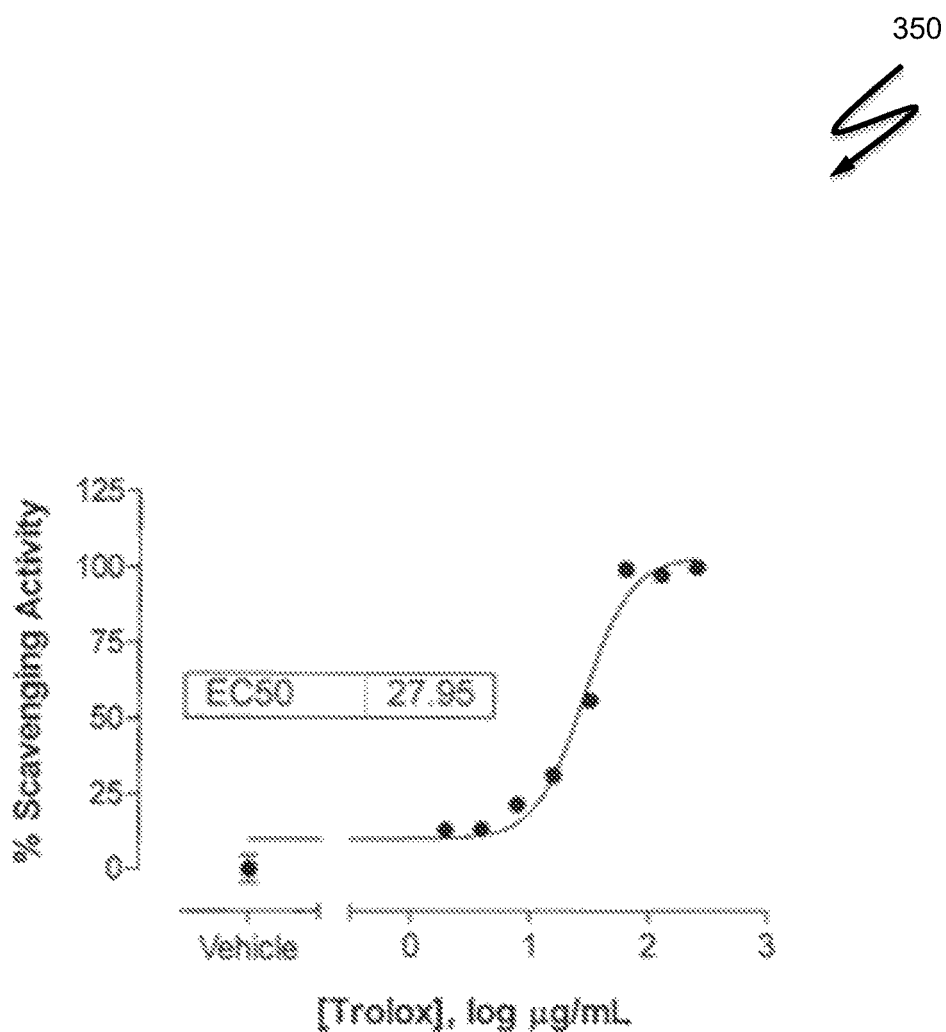
FIG. 3B illustrates a graph illustrating DPPH radical scavenging activity by the Trolox, by the herbal supplement composition 3 in accordance with one embodiment of the present invention.

FIG. 3A illustrates a graph illustrating DPPH radical scavenging activity by the supplement composition, and FIG. 3B illustrates a graph illustrating DPPH radical scavenging activity by the Trolox, in accordance with one embodiment of the present invention. Particularly, the supplement composition illustrates dose-dependent DPPH scavenging activity, with an $EC_{50}$ of 48 µg/mL. An increase in DPPH scavenging activity is also observed with Trolox, with an $EC_{50}$ of 28 µg/mL. Particularly, the error bars in FIG. 3A and FIG. 3B represent Mean±SEM. Table 3 below illustrates DPPH scavenging (% activity) as a function of Herbal supplement concentration.

TABLE 8

DPPH scavenging (% activity) as a function of Herbal Supplement Composition 3.

| Supplement, µg/mL | % Activity (Mean ± SEM) |
|---|---|
| 0 | 0 ± 0.5 |
| 0.78 | 9.86 ± 0.13 |
| 1.56 | 11.88 ± 0.12 |
| 3.13 | 10.53 ± 30.075 |
| 6.3 | 13.8 ± 0.2 |
| 12.5 | 15.27 ± 1.12 |
| 25 | 32.03 ± 0.28 |
| 50 | 45.77 ± 3.33 |
| 100 | 78.57 ± 0.18 |
| 200 | 94.8 ± 1.85 |
| 400 | 83.92 ± 1.72 |

Experiment 8: To Evaluate Effect of Herbal Supplement Composition 3 on COX-1 Enzyme Activity The objective of this experiment is to evaluate the effect of the supplement composition on COX-1 activity in a biochemical assay. Cyclooxygenase (COX), also known as prostaglandin-endoperoxide synthase (PTGS, EC 1.14.99.1), is a bi functional enzyme that shows both cyclooxygenase and peroxidase activity. Two isoforms of this enzyme are COX-1 and COX-2. Particularly, COX-1 is constitutively expressed in many tissues. COX-2 is not expressed under normal conditions in most cells, but elevated during disease conditions. Cyclooxygenase converts arachidonic acid to hydroperoxy endoperoxide PGG2, and COX's peroxidase activity further converts PGG2 to the corresponding alcohol, PGH2 with a loss of oxygen radical. The released oxygen can be quantitatively measured using the Ampiflu (ADHP) substrate and in turn the activity of the enzyme is calculated from fluorescence measurements.

The reagents used for this experiment are Cyclooxygenase 1 from sheep (Cat # C0733), Tris-HCl, EDTA, Hematin (Cat #51280), Arachidonic acid (Cat # A3611) and ADHP (10-Acetyl-3, 7-dihydroxyphenoxazine; Cat #90101) procured from Sigma-Aldrich. The supplement composition is dissolved in DMSO with sonication for 15 min and centrifuged at 10,000 rpm for 10 min at room temperature to remove insoluble debris. The reference compound used is Indomethacin (CAS: 53-86-1) and is dissolved in DMSO and used at 0.5, 5 and 50 µM concentrations. The assay is run in a 384 well format in a final volume of 20 µL. The enzyme is taken in Tris-HCl buffer (pH 8.0) containing EDTA (3 µM) and Hematin (15 µM). The enzyme is treated with or without different concentrations of the supplement or the standard Indomethacin and incubated for 10 min. At the end of 10 minutes, Arachidonic acid (100 µM) and ADHP (30 µM) are mixed and added to the reaction mixture.

After 5 minutes, the enzyme activity is calculated from the fluorescence measurements (Ex 535 nm, Ex 587 nm). The DMSO concentration in the assay is maintained at less than equal to 1.0%. The data is fit to a non-linear regression using Graph pad Prism (version 5.0). The half maximal inhibitory concentration ($IC_{50}$) is obtained from the sigmoidal dose response and variable slope curve is generated. Statistical analyses are carried out using a one-way ANOVA followed by a Dunnett's multiple comparison test.

Figure 4A:
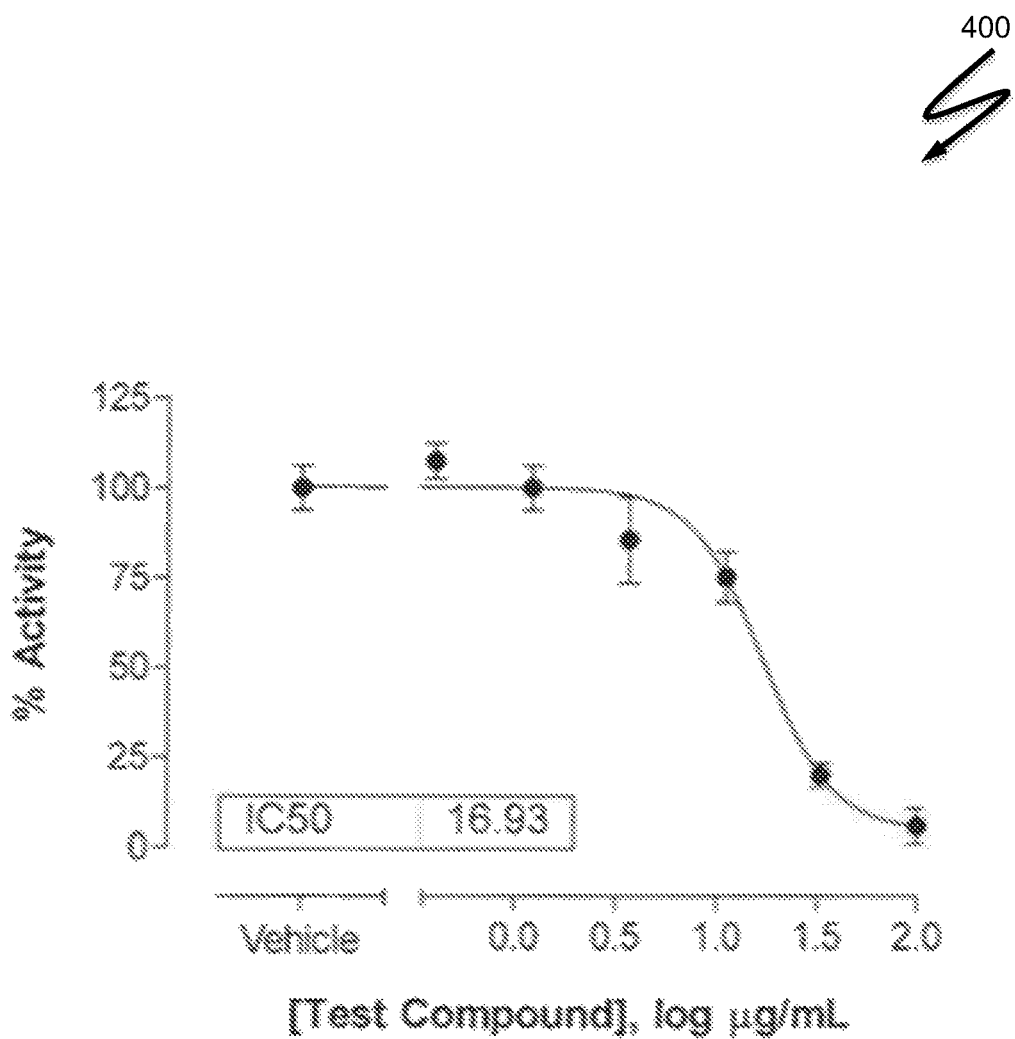
FIG. 4A illustrates a graph illustrating inhibition of COX-1 activity by the herbal supplement Composition 3, in accordance with one embodiment of the present invention.
Figure 4B:
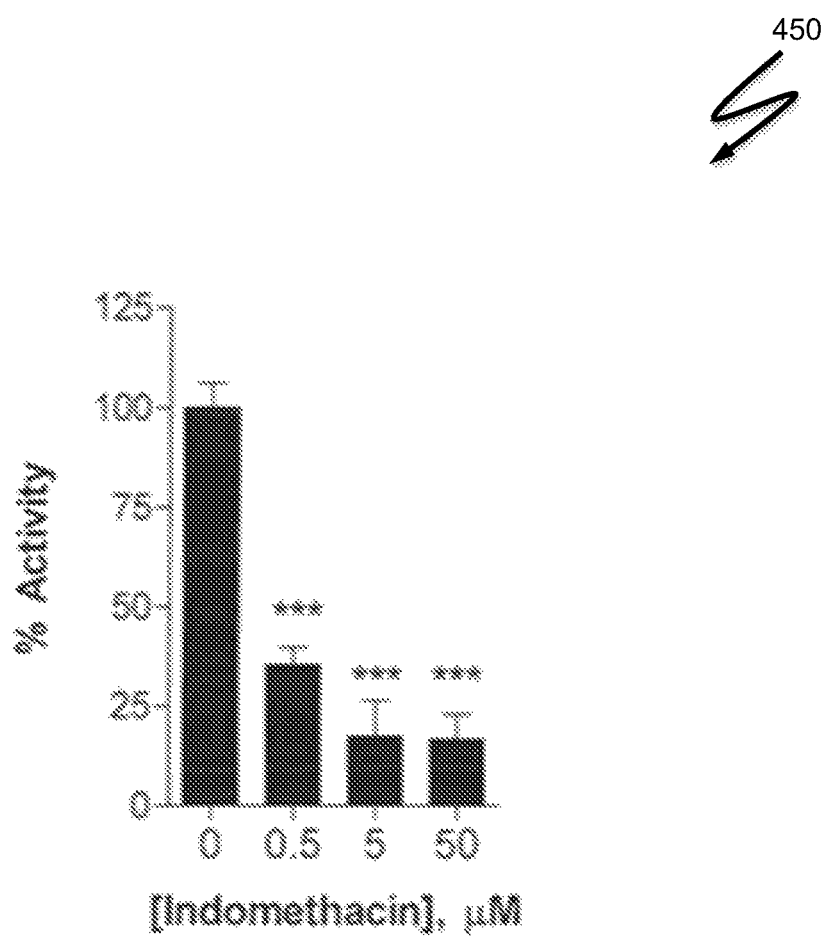
FIG. 4B illustrates a graph illustrating inhibition of COX-1 activity by Indomethacin by the herbal supplement composition 3 in accordance with one embodiment of the present invention.

FIG. 4A illustrates a graph illustrating inhibition of COX-1 activity by the supplement composition, in accordance with one embodiment of the present invention. Particularly, the test supplement showed significant inhibition of COX-1 activity with an $IC_{50}$ of 17 µg/mL. FIG. 4B illustrates a graph illustrating inhibition of COX-1 activity by Indomethacin, in accordance with one embodiment of the present invention. The standard inhibitor, Indomethacin, showed significant inhibition of COX-1 activity at 0.5, 5 and 50 µM. The error bars in FIG. 4A and FIG. 4B represent Mean±SEM, where *P<0.001, P<0.01, *P<0.05, and one-way ANOVA followed by Dunnett's test. Table 4 below illustrates COX-1 activity (% activity) as a function of test supplement concentration.

TABLE 9

COX-1 activity (% activity) as a function of Herbal Supplement Composition 3

| Supplement, µg/mL | % Activity (Mean ± SEM) |
|---|---|
| 0 | 100 ± 6.2 |
| 0.41 | 107.4 ± 4.97 |
| 1.23 | 100 ± 6.2 |
| 3.7 | 85.48 ± 12.1 |
| 11.1 | 75.16 ± 7.07 |
| 33.3 | 19.84 ± 3.39 |
| 100 | 5.81 ± 4.84 |

Experiment 9: To Evaluate Effect of Herbal Supplement Composition 3 on COX-2 Enzyme Activity The objective of the experiment is to evaluate the effect of the Herbal supplement composition on COX-2 activity in a biochemical assay. The reagents used for the evaluation are recombinant Cyclooxygenase 2 (Cat # C0858), Tris-HCl, EDTA, Hematin (Cat #51280), Arachidonic acid (Cat # A3611) and ADHP (10-Acetyl-3, 7-dihydroxyphenoxazine; Cat #90101), which are procured from Sigma-Aldrich.

Firstly, the supplement is dissolved in DMSO with sonication for 15 min and centrifuged at 10,000 rpm for 10 min at room temperature to remove insoluble debris. The reference compound used is Indomethacin (CAS: 53-86-1) and the same is dissolved in DMSO and used at 0.5, 5 and 50 µM concentrations. The assay is run in a 384 well format in a final volume of 20 µL. The enzyme is taken in Tris-HCl buffer (pH 8.0) containing EDTA (3 µM) and Hematin (15 µM). The enzyme is treated with or without different concentrations of the test supplement or the standard Indomethacin and incubated for 10 min. At the end of 10 minutes, Arachidonic acid (100 µM) and ADHP (30 µM) are mixed and added to the reaction mixture. After 5 minutes, enzyme activity is calculated from the fluorescence measurements (Ex 535 nm, Em 587 nm). The DMSO concentration in the assay is maintained at less than equal to 1.0%. The data is fit to a non-linear regression using Graph pad Prism (version 5.0). The half maximal inhibitory concentration ($IC_{50}$) is obtained from the sigmoidal dose response and a variable slope curve is generated. Statistical analyses are carried out using a one-way ANOVA followed by a Dunnett's multiple comparison test.

Figure 5A:
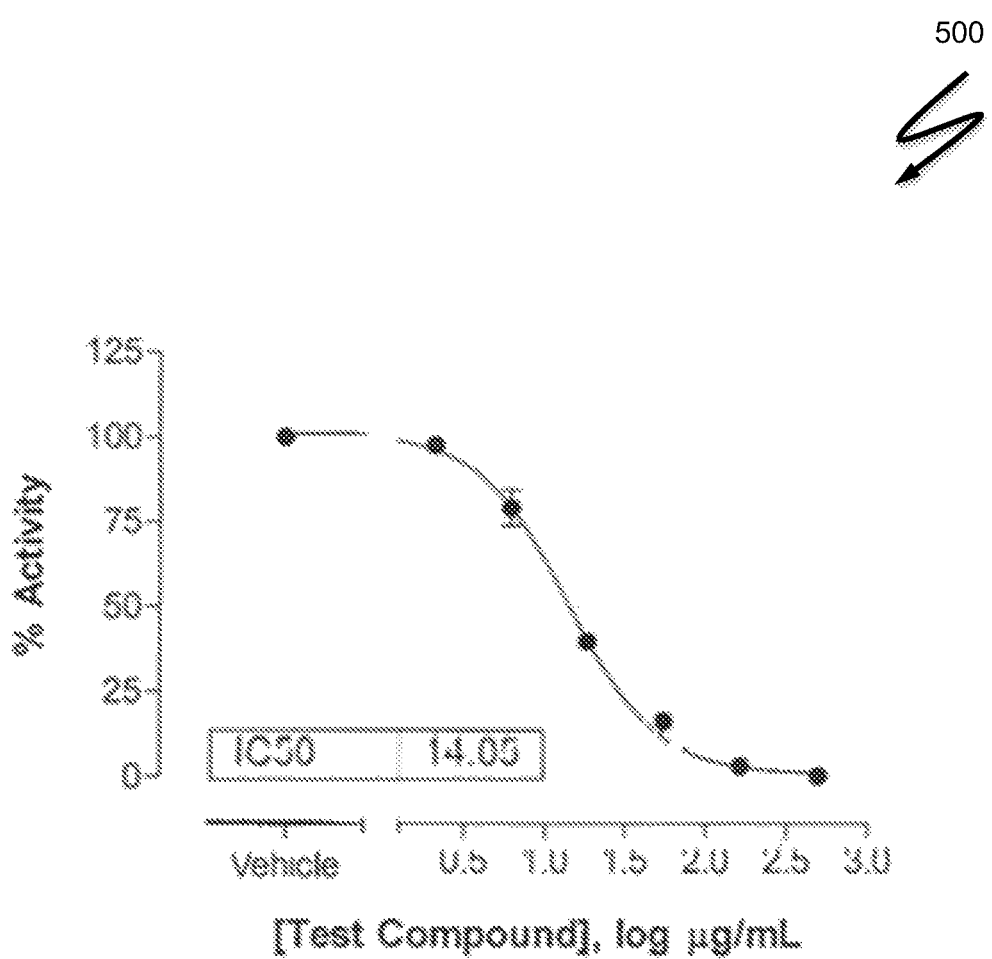
FIG. 5A illustrates a graph illustrating inhibition of COX-2 activity by the by the herbal supplement composition 3, in accordance with one embodiment of the present invention.
Figure 5B:
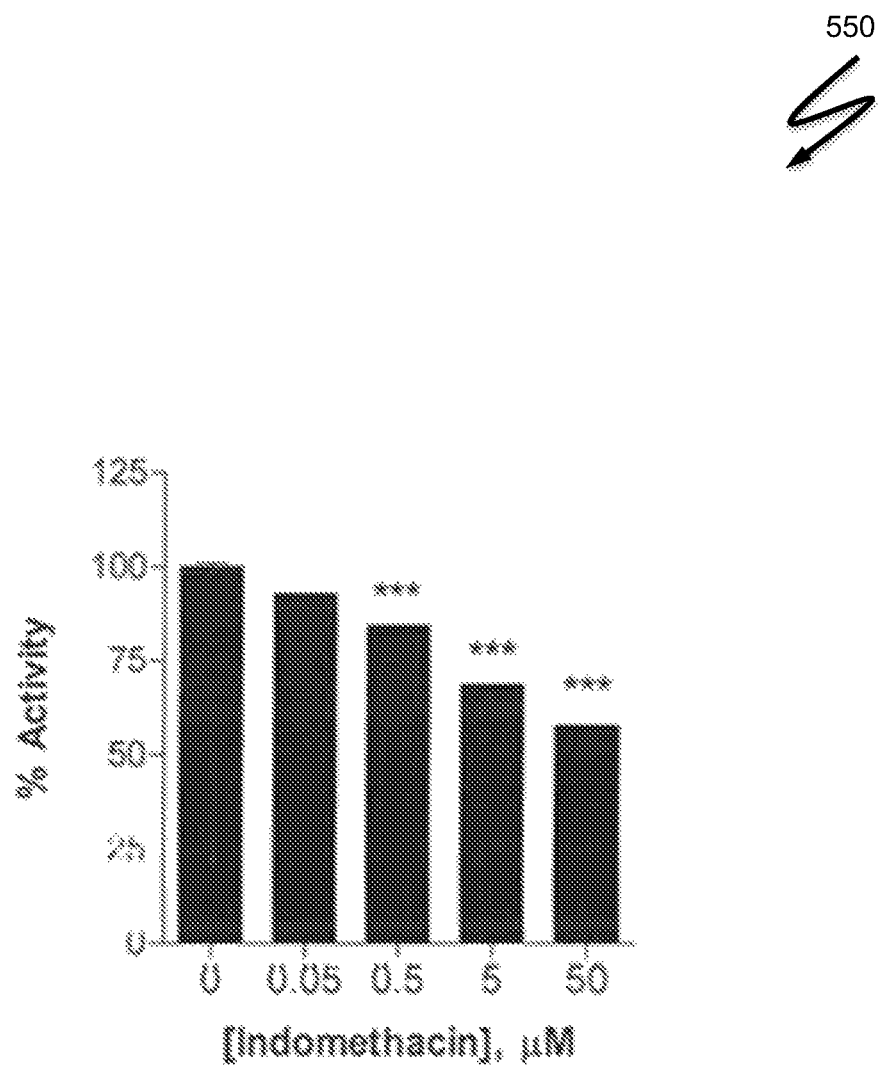
FIG. 5B illustrates a graph illustrating inhibition of COX-2 activity by Indomethacin by the herbal supplement composition 3 in accordance with one embodiment of the present invention.

FIG. 5A illustrates a graph illustrating inhibition of COX-2 activity by supplement composition, in accordance with one embodiment of the present invention. The supplement composition illustrates significant inhibition of COX-2 activity with an $IC_{50}$ of 14 µg/mL. FIG. 5B illustrates a graph illustrating inhibition of COX-2 activity by Indomethacin, in accordance with one embodiment of the present invention. The standard inhibitor Indomethacin illustrates significant inhibition of COX-2 activity at 0, 5, 5 and 50 µM. The error bars represent Mean±SEM where, *P<0.001, P<0.01, *P<0.05, and one-way ANOVA is followed by Dunnett's test. Table 5 below illustrates COX-2 activity (% activity) as a function of Herbal supplement concentration.

TABLE 10

COX-2 activity (% activity) as a function of Herbal Supplement Composition 3

| Supplement, µg/mL | % Activity (Mean ± SEM) |
|---|---|
| 0 | 100 ± 0.88 |
| 2.1 | 97.67 ± 1.9 |
| 6.2 | 79.48 ± 5.18 |
| 18.5 | 40.96 ± 0.52 |
| 55.6 | 18.16 ± 1.3 |
| 166.7 | 5.1 ± 0.15 |
| 500 | 2.25 ± 1.1 |

Experiment 10: To Evaluate the Effect of Herbal Supplement Composition 3 LDL Oxidation in a Cell-Free System The objective of the experiment is to evaluate the effect of the test supplement on LDL oxidation in a cell-free system. Cardiovascular disease (CVD) is the leading cause of death in developed countries. Atherosclerosis is a response of blood vessels to injury at the beginning of the formation of an atherosclerotic plaque. Low-density lipoprotein (LDL) is a major cholesterol carrier in the bloodstream, and the concentration of LDL cholesterol is directly correlated with the incidence of CVD. Increased oxidized LDL (OxLDL) acts as an atherogenic factor by triggering an inflammatory process. OxLDL can induce cell activation, secretion of inflammatory mediators, and expression of adhesion molecules. The reagents used are Lipoproteins, Low Density, Human Plasma and Atorvastatin.

The Herbal supplement composition is dissolved in DMSO with sonication for about 15 min and centrifuged at 10,000 rpm for 10 min at room temperature to remove insoluble debris. The reference compound for the present experiment is Atorvastatin (CAS: 134523-03-8) and is dissolved in DMSO. Atorvastatin is used at different concentrations and used as positive control. LDL samples of about 50 µg protein/mL are pre-incubated at 37° C. in a medium containing 10 mM phosphate buffer having pH 7.4 with different supplement concentrations.

After 5 minutes oxidation is initiated by the addition of $CUSO_4$ at 25 µM. The results are monitored by measuring the increase in absorbance at 234 nm due to conjugated diene (CD) formation for 5 hours in kinetic mode. The DMSO concentration in the assay is maintained at less than equal to 1.0%. The data is fit to a non-linear regression using Graph pad Prism (version 5.0). The half maximal inhibitory concentration ($IC_{50}$) is obtained from the sigmoidal dose response and variable slope curve is generated. Statistical analyses are carried out using a one-way ANOVA followed by a Dunnett's multiple comparison test. Moreover, the data represent five replicates for each condition.

Figure 6A:
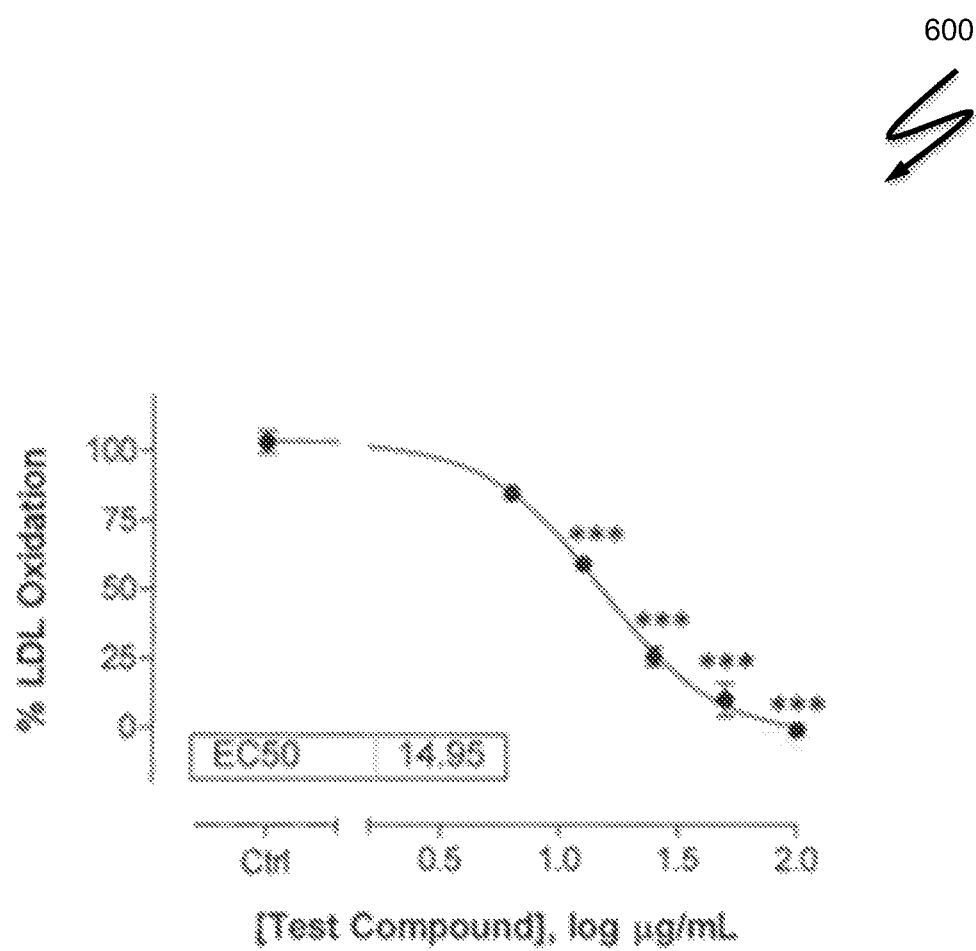
FIG. 6A illustrates a graph illustrating inhibition of LDL oxidation by the herbal supplement composition 3 in accordance with one embodiment of the present invention.

FIG. 6A illustrates a graph illustrating inhibition of LDL oxidation by the Herbal supplement composition, in accordance with one embodiment of the present invention. As illustrated in the graph, the supplement composition significantly inhibited LDL oxidation caused by $Cu^{2+}$ ions in a dose-dependent manner with an $EC_{50}$ of 15 µg/mL.

Figure 6B:
FIG. 6B illustrates a graph illustrating inhibition of LDL oxidation by Atorvastatin and ascorbic acid by the herbal supplement composition 3 in accordance with one embodiment of the present invention.
Figure 6B:
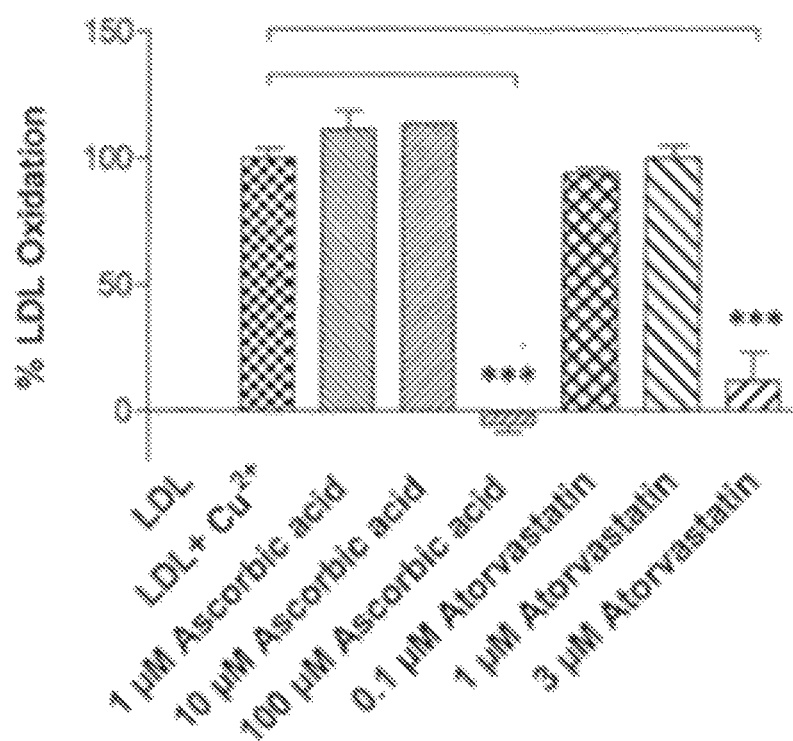
Figure 7:
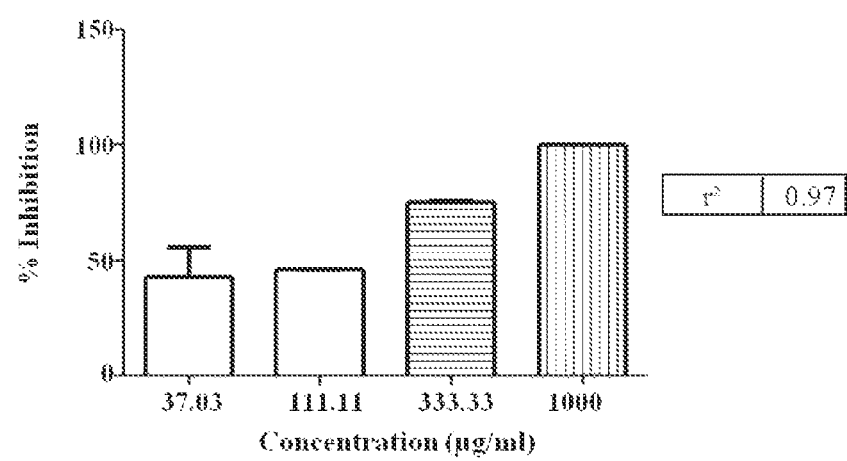
FIG. 07 illustrates a graph illustrating inhibition of LDL oxidation by the herbal supplement composition 2, in accordance with one embodiment of the present invention.
Figure 8A:
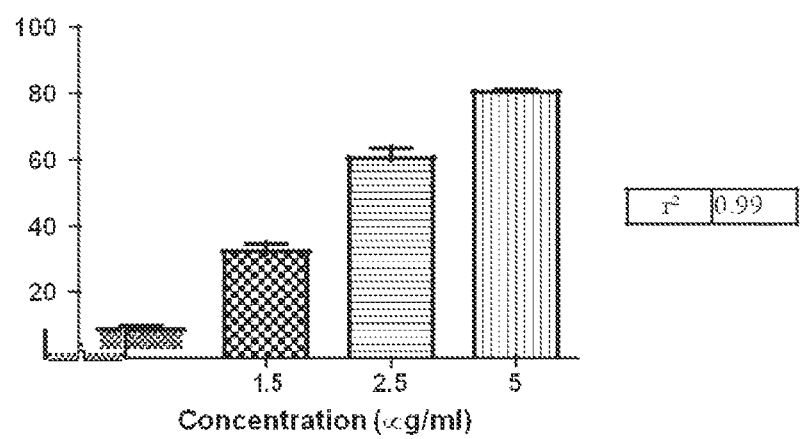
FIG. 08A illustrates a graph illustrating Increase in DPPH radical scavenging activity by the herbal supplement composition 2, in accordance with one embodiment of the present invention.
Figure 8B:
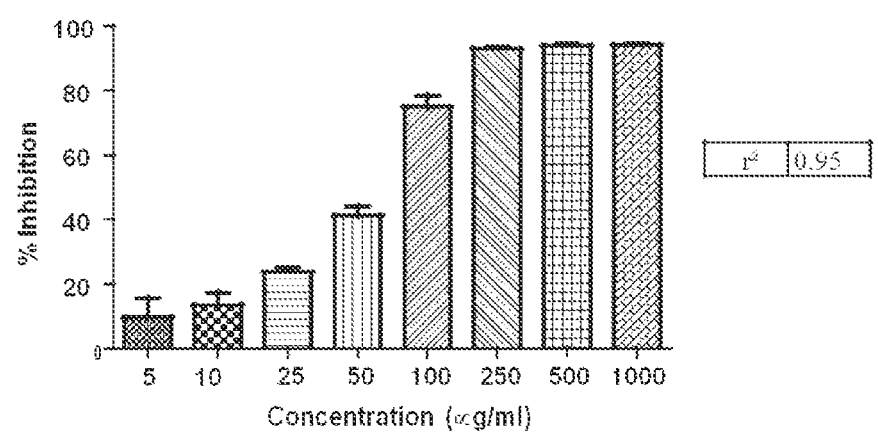
FIG. 08B illustrates a graph illustrating Increase in DPPH radical scavenging activity by the Trolox, in accordance with one embodiment of the by the herbal Supplement composition 2.
Figure 9A:
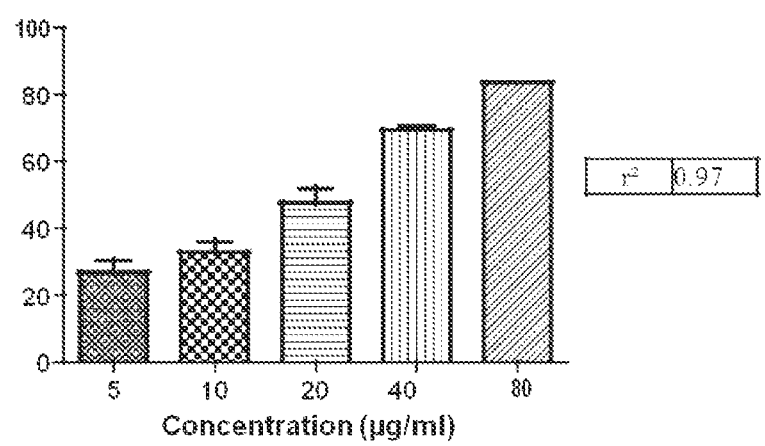
FIG. 9A illustrates a graph illustrating effect of Gallic acid on super oxide radicals scavenging activity by the herbal supplement composition 2 and, FIG. 9B illustrates a graph illustrating effect of herbal Supplement composition 2 on super oxide radicals scavenging activity in accordance with one embodiment of the present invention.
Figure 9B:
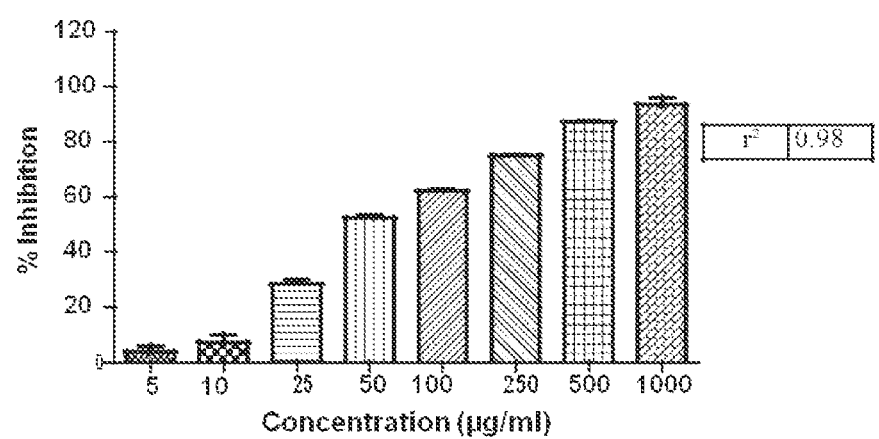

FIG. 6B illustrates a graph illustrating inhibition of LDL oxidation by Atorvastatin and ascorbic acid, in accordance with one embodiment of the present invention. A significant inhibition of LDL oxidation is also observed with Atorvastatin and ascorbic acid. The error bars in FIG. 6A & FIG. 6B represent Mean±SEM where, *$P<0.001$, $P<0.01$, *$P<0.05$, and one-way ANOVA is followed by Dunnett's test. Table 11 below illustrates data related to LDL oxidation (% activity) as a function of supplement concentration.

TABLE 11

LDL oxidation (% activity) as a function of Herbal Supplement Composition 3

| Supplement, µg/mL | % Activity (Mean ± SEM) |
|---|---|
| 0 | 103 ± 4 |
| 6.25 | 84.5 ± 1.5 |
| 12.5 | 59 ± 3 |
| 25 | 25.5 ± 3.5 |
| 50 | 10 ± 6 |
| 100 | −1 ± 2 |

Experiment 11: To Evaluate ORAC(Oxygen Radical Absorbance Capacity) of Herbal Supplement Composition 3

The Objective of the experiment is to Evaluate ORAC (Oxygen Radical Absorbance Capacity) of Herbal Supplement composition. Oxygen Radical Absorbance Capacity (ORAC) tests are among the most acknowledged methods that measure antioxidant scavenging activity against oxygen radicals that are known to be involved in the pathogenesis of aging and many common diseases. ORAC 6.0 consists of six types of ORAC assays that evaluate the antioxidant capacity of a material against six primary reactive oxygen species (ROSs, commonly called "oxygen radicals") found in humans: peroxyl radical, hydroxyl radical, superoxide anion, singlet oxygen, peroxynitrite and hypochlorite. This is a comprehensive panel that evaluates the antioxidant capacity of a material against oxygen radicals The ORAC tests are based on evaluating the capacity of an interested material to protect a probe (a fluorescent probe or chromagen) from its damage by ROSs. In all ORAC assays, an ROS inducer is introduced to the assay system. The ROS inducer triggers the release of a specific ROS, which would degrade the probe and cause its emission wavelength or intensity change. When an antioxidant material presents in the environment, the antioxidant absorbs the ROS and preserves the probe from degradation. The degree of probe preservation indicates the antioxidant capacity of the material. Trolox is used as the reference standard, and the results are expressed as µmole Trolox equivalency per gram (or milliliter) of a tested material.

TABLE 12

ORAC Score (Oxygen Radical Absorbance Capacity) of Herbal Supplement composition 3 against free radicals

| Radicals | Result |
|---|---|
| ORAC against peroxyl radicals | 3,930 µmole TE/serving size |
| ORAC against hydroxyl radicals | 14,246 µmole TE/serving size |
| ORAC against peroxynitrite | 597 µmole TE/serving size |
| ORAC against super oxide anion | 6,243 µmole TE/serving size |
| ORAC against singlet oxygen | 20,691 µmole TE/serving size |
| ORAC against hypochlorite | 4,449 µmole TE/serving size |

There are six predominant reactive species found in the body: peroxyl radicals, hydroxyl radicals, peroxynitrite, super oxide anion, singlet oxygen and hypochlorite. ORAC 6.0 provides a measure of the total antioxidant power of a food/nutrition product against the six predominant reactive species. The ORAC result is expressed as micromole Trolox equivalency (µmole TE) per gram. Serving size=2.17 g Therefore, as may be seen, embodiments of the present invention a herbal composition provide a health supplement for total body health needs. The present supplement can be consumed by anyone who has attained the age of 17 years. In-vivo and in-vitro studies conducted on the herbal composition 3 shows efficacy. The present herbal composition supplement has high antioxidant activity and insulin resistance activity through ORAC study and DPPH radical scavenging activity. Therefore, the present composition has been found to be useful towards improving health and enhancing the ability to overcome various disease conditions naturally. Moreover, the present supplement bypasses the need of intake of different dietary supplements to reap the same type of health benefits. The present invention is a broadspectrum antioxidant, antiviral, and antibacterial herbal composition supplement.

Accordingly, while there has been shown and described the preferred embodiment of the invention is to be appreciated that the invention may be embodied otherwise than is herein specifically shown and described and, within said embodiment, certain changes may be made in the form and arrangement of the parts without departing from the underlying ideas or principles of this invention within the scope of the claims appended herewith.

In one embodiment, the herbal composition 1 is provided to reduce oxidative stress, comprising therapeutically effective amounts of *Moringa Oleifera* Leaf Powder, Oregano Vulgare Leaf Extract, Shilajit extract, Spirulina, Amla fruit extract, and Piperine extract.

In one embodiment, the herbal composition 1 includes 40% to 42% by weight of *Moringa Oleifera* Leaf Powder, 21% to 23% by weight of Oregano Vulgare Leaf Extract, 10% to 12% by weight of Shilajit Extract, 10% to 12% by weight of Spiriluna, 12% to 14% by weight of Amla Extract, and 0.5% to 1% by weight of Piperine Extract.

In one embodiment, the herbal composition 1 further includes about 41.43% by weight of *Moringa Oleifera* Leaf powder.

In one embodiment, the herbal composition 1 further includes about 22% by weight of Oregano Vulgare Extract powder.

In one embodiment, the herbal composition 1 further includes about 11% by weight of Shilajit Extract powder.

In one embodiment, the herbal composition 1 further includes about 11% by weight of Spirulina powder.

In one embodiment, the herbal composition 1 further includes about 13.81% by weight of Amla fruit Extract powder.

In one embodiment, the herbal composition 1 further includes about 0.55% by weight of Piperine Extract powder.

In one embodiment, the herbal composition as discussed herein is administered orally.

In accordance with an embodiment of the present invention, the herbal composition as discussed herein in the form of a capsule.

In one embodiment, the herbal composition 1 further includes a high Oxygen Radical Absorbance Capacity (ORAC) value, wherein the ORAC value of a serving of the composition against peroxyl radicals 5,219 µmole TE/2 g. In one embodiment, the herbal composition 1 further includes a high Oxygen Radical Absorbance Capacity (ORAC) value, wherein the ORAC value of a serving of the composition against hydroxyl radicals 10,964 µmole TE/2 g. In one embodiment, the herbal composition 1 further includes a high Oxygen Radical Absorbance Capacity (ORAC) value, wherein the ORAC value of a serving of the composition against peroxynitrite radicals 543 µmole TE/2 g. In one embodiment, the herbal composition 1 further includes a high Oxygen Radical Absorbance Capacity (ORAC) value, wherein the ORAC value of a serving of the composition against super oxide anion radicals 3,924 µmole TE/2 g.

In one embodiment, the herbal composition 1 further includes a high Oxygen Radical Absorbance Capacity (ORAC) value, wherein the ORAC value of a serving of the composition against singlet oxygen radicals 392 µmole TE/2 g. In one embodiment, the herbal composition 1 further includes therapeutically effective amounts of *Moringa Oleifera* Leaf Powder, Oregano Vulgare Leaf Extract, Shilajit extract, Rosemary Leaf Extract, Pomegranate Peel Extract Spirulina, Amla fruit extract, Piperine extract.

In one embodiment, the herbal composition 1 further includes 27% to 28% by weight of *Moringa Oleifera* Leaf Powder, 13% to 15% by weight of Oregano Vulgare Leaf Extract, 6% to 8% by weight of Rosemary Leaf Extract, 10% to 12% by weight of Pomegranate Peel Extract, 10% to 12% by weight of Shilajit Extract, 10% to 12% by weight of Spiriluna, 13% to 15% by weight of Amla Extract, 0.5% to 1% by weight of Piperine Extract.

In one embodiment, the herbal composition 1 further includes about 27.6% by weight of *Moringa Oleifera* Leaf powder.

In one embodiment, the herbal composition 1 further includes about 13.81% by weight of Oregano Vulgare Extract powder.

In one embodiment, the herbal composition 1 further includes about 11% by weight of Shilajit Extract powder.

In one embodiment, the herbal composition 1 further includes about 11% by weight of Spirulina powder.

In one embodiment, the herbal composition 1 further includes about 13.81% by weight of Amla fruit Extract powder.

In one embodiment, the herbal composition 1 further includes about 11% by weight of Rosemary Leaf Extract powder.

In one embodiment, the herbal composition 1 further includes about 11% by weight of Pomegranate Peel Extract powder.

In one embodiment, the herbal composition 1 further includes about 0.52% by weight of Piperine Extract powder.

In accordance with an embodiment of the present invention, a herbal composition 3 to reduce oxidative stress and Inflammation, includes therapeutically effective amounts of *Moringa Oleifera* Leaf Powder, Oregano Vulgare Leaf Extract, Shilajit extract, Rosemary Leaf Extract, Pomegranate Peel Extract Spirulina, Amla fruit extract, Fenugreek seed extract, Curcuma longa extract, Piperine extract.

In one embodiment, the herbal composition 3 further includes 26% to 28% by weight of *Moringa Oleifera* Leaf Powder, 6% to 8% by weight of Oregano Vulgare Leaf Extract, 6% to 8% by weight of Rosemary Leaf Extract, 6% to 8% by weight of Pomegranate Peel Extract, 10% to 12% by weight of Shilajit Extract, 10% to 12% by weight of Spiriluna, 10% to 12% by weight of Amla Extract, 15% to 16% by weight of Fenugreek seed Extract, 2% to 3% by weight of Curcuma longa Extract, 0.5% to 1% by weight of Piperine Extract.

In one embodiment, the herbal composition 3 further includes about 26.17% by weight of *Moringa Oleifera* Leaf powder.

In one embodiment, the herbal composition 3 further includes about 7.8% by weight of Oregano Vulgare Extract powder.

In one embodiment, the herbal composition 3 further includes about 10.4% by weight of Shilajit Extract powder.

In one embodiment, the herbal composition 3 further includes about 10.4% by weight of Spirulina powder.

In one embodiment, the herbal composition 3 further includes about 10.4% by weight of Amla fruit Extract powder.

In one embodiment, the herbal composition 3 further includes about 7.8% by weight of Rosemary Leaf Extract powder.

In one embodiment, the herbal composition 3 further includes about 7.8% by weight of Pomegranate Peel Extract powder.

In one embodiment, the herbal composition 3 further includes about 15.7% by weight of Fenugreek seed Extract powder.

In one embodiment, the herbal composition 3 further includes about 2.6% by weight of Curcuma Longa Extract powder.

In one embodiment, the herbal composition 3 further includes about 0.52% by weight of Piperine Extract powder.

PATENT REFERENCES

1. U.S. Pat. No. 6,541,045 (Alec Charters, James Selander, Shayne Morris, Robert Charles Thompson, Lori Blackner)
2. U.S. Pat. No. 6,264,995 (Thomas Newmark, Paul Schulick)
3. U.S. Pat. No. 6,042,834 (Mohamed Wasif Baraka)

NON PATENT CITATIONS

1. Russ, K. Antioxidants: The natural anti-inflammatory. 2014.
2. Reuter S, Gupta S C, Chaturvedi M M, Aggarwal B B. Oxidative stress, inflammation, and cancer: how are they linked? Free Radic Biol Med. 2010; 49(11):1603-16.
3. Duracková Z. Some current insights into oxidative stress. Physiol Res. 2010; 59(4):459-69.
4. Poyton R O, Ball K A, Castello P R. Mitochondrial generation of free radicals and hypoxic signaling. Trends Endocrinol Metab. 2009; 20(7):332-40.
5. Fridovich I. The biology of oxygen radicals. Science. 1978; 201(4359):875-80.
6. Goossens V, De Vos K, Vercammen D, Steemans M, Vancompernolle K, Fiers W, Vandenabeele P, Grooten J. Redox regulation of TNF signaling. Biofactors. 1999; 10(2-3):145-56.
7. Hussain S P, Hofseth L J, Harris C C. Radical causes of cancer. Nat Rev Cancer. 2003; 3(4):276-85.
8. Schraufstätter I, Hyslop P A, Jackson J H, Cochrane C G. Oxidant-induced DNA damage of target cells. J Clin Invest. 1988; 82(3):1040-50.
9. Visconti R, Grieco D. New insights on oxidative stress in cancer. Curr Opin Drug Discov Devel. 2009; 12(2):240-5.
10. Briganti S, Picardo M. Antioxidant activity, lipid peroxidation and skin diseases. What's new. J Eur Acad Dermatol Venereol. 2003; 17(6):663-9.
11. Chaturvedi N. The burden of diabetes and its complications: trends and implications for intervention. Diabetes Res Clin Pract. 2007 May; 76 Suppl 1( ):S3-12.
12. Brownlee M. Biochemistry and molecular cell biology of diabetic complications. Nature. 2001; 414(6865):813-20.
13. Godsey J, Grundmann O. Review of Various Herbal Supplements as Complementary Treatments for Oral Cancer. J Diet Suppl. 2016; 1-13, in press.
14. Kumar Gupta S, Kumar B, Srinivasan B P, et al. Retinoprotective effects of *Moringa oleifera* via antioxidant, anti-inflammatory, and anti-angiogenic mechanisms in streptozotocin-induced diabetic rats. J Ocul Pharmacol Ther. 2013 May; 29(4):419-26.
15. Fahey J W. *Moringa oleifera*: A review of the medical evidence for its nutritional, therapeutic, and prophylactic properties. Part 1. Trees for Life Journal 2005; 1:5.
16. Dragland S, Senoo H, Wake K, Holte K, Blomhoff R. Several Culinary and Medicinal Herbs Are Important Sources of Dietary Antioxidants. JNutr 2003; 133(5): 1286-1290.
17. Moreno S, Scheyer T, Romano C S, Vojnov A A. Antioxidant and antimicrobial activities of rosemary extracts linked to their polyphenol composition. Free Radic Res. 2006; 40(2):223-31.
18. Cheung S, Tai J. Anti-proliferative and antioxidant properties of rosemary *Rosmarinus officinalis*. Oncology Reports. 2007; 17(6):1525-31.
19.2—Peng C H, Su J D, Chyau C C, Sung T Y, Ho S S, Peng C C, Peng R Y. Supercritical fluid extracts of rosemary leaves exhibit potent anti-inflammation and anti-tumor effects. Biosci Biotechnol Biochem. 2007; 71(9):2223-32.
20.2—Fawole O A, Makunga N P, Opara U L. Antibacterial, antioxidant and tyrosinase-inhibition activities of pomegranate fruit peel methanolic extract. BMC Complement Altern Med. 201230; 12:200.
21. Neyrinck A M, Van Hee V F, Bindels L B, et al. Polyphenol rich extract of pomegranate peel alleviates tissue inflammation and hypercholesterolaemia in high-fat diet-induced obese mice: potential implication of the gut microbiota. Br J Nutr. 2013 Mar. 14; 109(5):802-9.
22. Poltanov E A, Shikov A N, Dorman H J, Pozharitskaya O N, Makarov V G, Tikhonov V P, Hiltunen R. Chemical and antioxidant evaluation of Indian gooseberry (*Emblica officinalis* Gaertn., syn. *Phyllanthus emblica* L.) supplements. Phytother Res. 2009; 23(9):1309-15.
23. Kim H J, Yokozawa T, Kim H Y, Tohda C, Rao T P, Juneja L R. Influence of amla (*Emblica officinalis* Gaertn.) on hypercholesterolemia and lipid peroxidation in cholesterol-fed rats. J Nutr Sci Vitaminol (Tokyo). 2005; 51(6):413-8.
24. Mahata S, Pandey A, Shukla S, Tyagi A, Husain S A, Das B C, Bharti A C. Anticancer activity of *Phyllanthus emblica* Linn. (Indian gooseberry): inhibition of transcription factor AP-1 and HPV gene expression in cervical cancer cells. Nutr Cancer. 2013; 65 Suppl 1:88-97.
25. Koshy S M, Bobby Z, Hariharan A P, Gopalakrishna S M. Amla (*Emblica officinalis*) extract is effective in preventing high fructose diet-induced insulin resistance and atherogenic dyslipidemic profile in ovariectomized female albino rats. Menopause. 2012; 19(10):1146-55.
26. D'souza J J, D'souza P P, Fazal F, Kumar A, Bhat H P, Baliga M S. Anti-diabetic effects of the Indian indigenous fruit *Emblica officinalis* Gaertn: active constituents and modes of action. Food Funct. 2014; 5(4):635-44.
27. Akhtar M S, Ramzan A, Ali A, Ahmad M. Effect of Amla fruit (*Emblica officinalis* Gaertn.) on blood glucose and lipid profile of normal subjects and type 2 diabetic patients. Int J Food Sci Nutr. 2011 September; 62(6):609-16. doi: 10.3109/09637486.2011.560565. Epub 2011 Apr. 18.
28. Reuter S, Gupta S C, Chaturvedi M M, Aggarwal B B. Oxidative stress, inflammation, and cancer: how are they linked? Free Radic Biol Med. 2010; 49(11):1603-16.
29. Mazokopakis E E, Starakis I K, Papadomanolaki M G, Mavroeidi N G, Ganotakis E S. The hypolipidaemic effects of Spirulina (*Arthrospira platensis*) supplementation in a Cretan population: a prospective study. J Sci Food Agric. 2014; 94(3):432-7.
30. Torres-Duran P V, Ferreira-Hermosillo A, Juarez-Oropezaco M A. Antihyperlipemic and antihypertensive effects of Spirulina *maxima* in an open sample of mexican population: a preliminary report. Lipids Health Dis. 2007; 6: 33.
31. Park H J, Lee Y J, Ryu H K, Kim M H, Chung H W, Kim W Y. A randomized double-blind, placebo-controlled study to establish the effects of spirulina in elderly Koreans. Ann Nutr Metab. 2008; 52(4):322-8.
32. Parikh P, Mani U, Iyer U. Role of Spirulina in the Control of Glycemia and Lipidemia in Type 2 Diabetes Mellitus. J Med Food. 2001; 4(4):193-199.
33. Ismail M, Hossain M F, Tanu A R, Shekhar H U. Effect of Spirulina Intervention on Oxidative Stress, Antioxidant Status, and Lipid Profile in Chronic Obstructive Pulmonary Disease Patients. Biomed Res Int. 2015; 2015: 486120.
34. Ku C S, Yang Y, Park Y, Jiyoung L. Health Benefits of Blue-Green Algae: Prevention of Cardiovascular Disease and Nonalcoholic Fatty Liver Disease. J Med Food. 2013; 16(2): 103-111.
35. Lee E H, Park J E, Choi Y J, Huh K P, Wha-Young K. A randomized study to establish the effects of spirulina in type 2 diabetes mellitus patients. Nutr Res Pract. 2008; 2(4): 295-300.
36. Kalafati M, Jamurtas A Z, Nikolaidis M G, Paschalis V, Theodorou A A, Sakellariou G K, Koutedakis Y, Kouretas D. Ergogenic and antioxidant effects of spirulina supplementation in humans. Med Sci Sports Exerc. 2010; 42(1): 142-51.
37. Tayyem R F, Heath D D, Al-Delaimy W K, Rock C L. Curcumin content of turmeric and curry powders. Nutr Cancer. 2006; 55(2):126-31.
38. Shoba G, Joy D, Joseph T, Majeed M, Rajendran R, Srinivas P S. Influence of piperine on the pharmacokinetics of curcumin in animals and human volunteers. Planta Med. 1998; 64(4):353-6.
39. Jurenka J S. Anti-inflammatory properties of curcumin, a major constituent of Curcuma longa: a review of preclinical and clinical research. Altern Med Rev. 2009; 14(2):141-53.

40. SinghS, Aggarwal B B. Activation of Transcription Factor N F-κB Is Suppressed by Curcumin (Diferuloylmethane). J Bio Chem. 1995; 270:24995-25000.
41. Marin Y E, Wall B A, Wang S, Namkoong J, Martino J J, Suh J, Lee H J, Rabson A B, Yang C S, Chen S, Ryu J H. Curcumin down regulates the constitutive activity of NF-kappaB and induces apoptosis in novel mouse melanoma cells. Melanoma Res. 2007; 17(5):274-83.
42. Chainani-Wu N. Safety and anti-inflammatory activity of curcumin: a component of tumeric (Curcuma longa). J Altern Complement Med. 2003 February; 9(1):161-8.
43. Goel A, Boland C R, Chauhan D P. Specific inhibition of cyclooxygenase-2 (COX-2) expression by dietary curcumin in HT-29 human colon cancer cells. Cancer Lett. 2001; 172(2):111-8.
44. Aggarwal B B, Harikumar K B. Potential therapeutic effects of curcumin, the anti-inflammatory agent, against neurodegenerative, cardiovascular, pulmonary, metabolic, autoimmune and neoplastic diseases. Int J Biochem Cell Biol. 2009; 41(1):40-59.
45. Bano G, Amla V, Raina R K, et al. The effect of piperine on pharmacokinetics of phenytoin in healthy volunteers. Planta Med 1987; 53:568-9.
46. Khardwaj R K, Glaeser H, Becquemont L, et al. Piperine, a major constituent of black pepper, inhibits human P-glycoprotein and CYP3A4. J Pharmacol Exp Ther 2002; 302:645-50.
47. Shrivastava P, Vaibhav K, Tabassum R, et al. Anti-apoptotic and anti-inflammatory effect of Piperine on 6-OHDA induced Parkinson's rat model. J Nutr Biochem. 2013 April; 24(4):680.
48. Ceriello A, Testa R. Antioxidant anti-inflammatory treatment in type 2 diabetes. Diabetes Care. 2009; 32 Suppl 2:S232-6.
49. Abourashed E A. Bioavailability of Plant-Derived Antioxidants. Antioxidants (Basel). 2013; 2(4):309-25
50. The Modifying Effects of Galactomannan from Canadian-Grown Fenugreek (*Trigonella foenum-graecum* L.) on the Glycemic and Lipidemic Status in Rats *Anchalee Srichamroen J Clin Biochem Nutr.* 2008 November; 43(3): 167-174.
51. Anti-Inflammatory Effects of Pomegranate Peel Extract in THP-1 Cells Exposed to Particulate Matter PM10-*Soojin Park* Evidence-Based Complementary and Alternative Medicine Volume 2016 (2016), Article ID 6836080

The invention claimed is:

1. A method of reducing oxidative stress in a human subject comprising administering to said subject in need thereof a therapeutically effective amount a herbal nutraceutical formulation,
   wherein the herbal nutraceutical formulation comprises the ingredients:
   (a) about 100-150 mg *Moringa Oleifera* Leaf Powder;
   (b) about 30 mg to 80 mg of Oregano Vulgare Leaf Extract;
   (c) about 30 mg to 40 mg of Rosemary Leaf Extract;
   (d) about 40 mg of Shilajit extract;
   (e) about 30 mg to 40 mg of Pomegranate Peel Extract;
   (f) about 40 mg of Spirulina;
   (g) about 40 mg to 50 mg of Amla fruit extract;
   (h) about 60 mg of Fenugreek seed extract;
   (i) about 10 g of Curcuma longa extract; and
   (j) about 2 mg of Pipeline extract.
2. The method of claim 1, wherein said ingredients are delivered in a capsule.
3. The method of claim 2, wherein said therapeutically effective amount is 4-6 capsules per serving size.

* * * * *

UNITED STATES PATENT AND TRADEMARK OFFICE
CERTIFICATE OF CORRECTION

| | | |
|---|---|---|
| PATENT NO. | : 10,967,025 B2 | Page 1 of 1 |
| APPLICATION NO. | : 15/563617 | |
| DATED | : April 6, 2021 | |
| INVENTOR(S) | : Karen Vieira | |

It is certified that error appears in the above-identified patent and that said Letters Patent is hereby corrected as shown below:

On the Title Page

Item (12) should now read:
Britto et al.

The correct inventorship should include two inventors, as listed below:
Full Name and Address of the Inventor 1:
JOHN BRITTO
Hiranandani Upscale
2302, Bayview Tower, OMR,
Egattur, Chennai 603103, India Full Name and Address of the Inventor 2:
KAREN VIEIRA
9314 Forest Hill Blvd Ste 6,
West Palm Beach, Florida 33411, US Signed and Sealed this
Twenty-fifth Day of February, 2025

Coke Morgan Stewart
*Acting Director of the United States Patent and Trademark Office*